US012761226B2

(12) United States Patent
Hernández Jiménez et al.

(10) Patent No.: US 12,761,226 B2
(45) Date of Patent: Oct. 13, 2026

(54) METHOD AND KIT FOR THE EARLY DETECTION OF SEPSIS

(71) Applicants: LOOP DIAGNOSTICS, S.L., Soria (ES); FUNDACIÓ INSTITUT D'INVESTIGACIÓ BIOMÈDICA DE BELLVITGE (IDIBELL), Barcelona (ES)

(72) Inventors: Enrique Hernández Jiménez, Barcelona (ES); Raoul Jansen, Hulsberg (NL); Joan Sabater Riera, Barcelona (ES)

(73) Assignees: LOOP DIAGNOSTICS, S.L., Soria (ES); FUNDACIÓ INSTITUT D'INVESTIGACIÓ BIOMEDICA DE BELLVITGE (IDIBELL), Barcelona (ES)

(*) Notice: Subject to any disclaimer, the term of this patent is extended or adjusted under 35 U.S.C. 154(b) by 828 days.

(21) Appl. No.: 17/928,741

(22) PCT Filed: May 31, 2021

(86) PCT No.: PCT/EP2021/064544
§ 371 (c)(1),
(2) Date: Nov. 30, 2022

(87) PCT Pub. No.: WO2021/245025
PCT Pub. Date: Dec. 9, 2021

(65) Prior Publication Data

US 2023/0236205 A1 Jul. 27, 2023

(30) Foreign Application Priority Data

Jun. 1, 2020 (EP) .................................... 20382462

(51) Int. Cl.
*G01N 33/543* (2006.01)
*G01N 33/68* (2006.01)

(52) U.S. Cl.
CPC ..... *G01N 33/6893* (2013.01); *G01N 33/6869* (2013.01); *G01N 2333/52* (2013.01); *G01N 2400/50* (2013.01); *G01N 2800/26* (2013.01); *G01N 2800/382* (2013.01)

(58) Field of Classification Search
None
See application file for complete search history.

(56) References Cited

U.S. PATENT DOCUMENTS

| | | | | |
|---|---|---|---|---|
| 5,262,296 | A | 11/1993 | Ogawa et al. | |
| 5,420,016 | A * | 5/1995 | Boguslaski .............. | C12Q 1/04 435/12 |
| 5,480,792 | A | 1/1996 | Buechler et al. | |
| 5,525,524 | A | 6/1996 | Buechler et al. | |
| 5,631,171 | A | 5/1997 | Sandstrom et al. | |
| 5,679,526 | A | 10/1997 | Buechler et al. | |
| 5,824,799 | A | 10/1998 | Buechler et al. | |
| 5,851,776 | A | 12/1998 | Walkirs | |
| 5,885,527 | A | 3/1999 | Buechler | |
| 5,922,615 | A | 7/1999 | Nowakowski et al. | |
| 5,939,272 | A | 8/1999 | Buechler et al. | |
| 5,947,124 | A | 9/1999 | Buechler et al. | |
| 5,955,377 | A | 9/1999 | Maul et al. | |
| 5,985,579 | A | 11/1999 | Buechler et al. | |
| 6,019,944 | A | 2/2000 | Buechler | |
| 6,113,855 | A | 9/2000 | Buechler | |
| 6,143,576 | A | 11/2000 | Buechler | |
| 2004/0018528 | A1 * | 1/2004 | Morimoto .............. | C12Q 1/485 435/7.1 |
| 2004/0106142 | A1 | 6/2004 | Ivey et al. | |
| 2005/0036943 | A1 * | 2/2005 | Broughton ......... | G01N 33/6863 424/9.1 |
| 2008/0299538 | A1 * | 12/2008 | Goodrich ............ | A61M 1/3683 604/410 |
| 2013/0216542 | A1 * | 8/2013 | Siadak .................. | A61K 47/60 424/139.1 |

(Continued)

FOREIGN PATENT DOCUMENTS

WO WO-2012019041 A2 * 2/2012 ........... A61K 40/416

OTHER PUBLICATIONS

Martins et al., Analysis of Proinflammatory and Anti-Inflammatory Cytokine Serum Concentraiton in Patients With Multiple Scleroiss by Using a Multiplexed Immunoassay, Am J Clin Pathol, 2011, 136, pp. 696-704. (Year: 2011).*

Harry Moscovitz, MD et al., "Plasma cytokine determinations in emergency department patients as a predictor of bacteremia and infectious disease severity," Critical Care Medicine, Jul. 1994, pp. 1, 102-1,107, vol. 22, No. 7.

Travis L. Holloway et al. "Toll-like receptor responses are suppressed in trauma ICU patients," Journal of Surgical Research, Nov. 1, 2016, pp. 139-145, vol. 206, No. 1.

Milena Karina Colo Brunialti et al., "Influence of EDTA and heparin on lipopolysaccharide binding and cell activation, evaluated at single-cell level in whole blood," Cytometry (Clinical Cytometry), Feb. 15, 2002, pp. 14-18, vol. 50, No. 1.

(Continued)

*Primary Examiner* — Gary Counts
(74) *Attorney, Agent, or Firm* — Pilloff Passino & Cosenza LLP; Rachel Pilloff; Sean Passino

(57) ABSTRACT

In vitro methods for detecting bacteremia, for selecting a therapy for a subject with cystic fibrosis or for a subject with systemic inflammatory response syndrome and for selecting a subject with cystic fibrosis or with systemic inflammatory syndrome for a particular therapy based on the expression levels of a gene selected from tumor necrosis factor alpha (TNFα), IL-1b, IL-10, CCL2, interferon beta (IFN-β), IL-17, IL-2, IL-4 and VEGF in a blood sample from the subject. Also provided is a kit comprising a TLR-4 agonist and a reagent specific for determining the level of at least one cytokine selected from the group consisting of tumor necrosis factor alpha (TNFα), IL-1b, IL-10, CCL2, interferon beta (IFN-β), IL-17, IL-2, IL-4 and VEGF and to the uses of this kit.

18 Claims, 11 Drawing Sheets

(56) References Cited

U.S. PATENT DOCUMENTS

| | | | | |
|---|---|---|---|---|
| 2014/0045825 A1* | 2/2014 | Leahy | C07D 487/04 514/249 | |
| 2021/0031184 A1* | 2/2021 | Bailey | B01L 3/5029 | |

OTHER PUBLICATIONS

P. Szodoray et al., "Circulating Cytokines in Primary Sjogren's Syndrome Determined by a Multiplex Cytokine Array System," Scandinavian Journal of Immunology, Jun. 1, 2004, pp. 592-599, vol. 59, No. 6.

Jessica Z. Kubicek-Sutherland et al., "Direct detection of bacteremia by exploiting host-pathogen interactions of lipoteichoic acid and lipopolysaccharide, "Scientific Reports, Apr. 17, 2019, vol. 9, No. 1.

Kathryn E Hally et al., "Platelets regulate leucocyte responses to Toll-like receptor stimulation," Clinical & Translational Immunology, Jan. 1, 2018, vol. 7, No. 7.

Reinaldo Salomao et al., "Lipopolysaccharide-cell interaction and induced cellular activation in whole blood of septic patients," Journal of Endotoxin Research, Oct. 1, 2002, pp. 371-379, vol. 8, No. 5.

Guadalupe Martin et al., "Role of plasma matrix-metalloproteases (MMPs) and their polymorphisms (SNPs) in sepsis development and outcome in ICU patients," Scientific Reports, May 16, 2014, vol. 4, No. 1.

Ping Zhang et al., "The Lineage-c-Kit+Sca-1+ Cell Response to Escherichia coli Bacteremia in Balb/c Mice," Stem Cells, Jul. 1, 2008, pp. 1,778-1,786, vol. 26, No. 7.

Sanne Van Den Berg et al., "Distinctive Cytokines as Biomarkers Predicting Fatal Outcome of Severe *Staphylococcus aureus* Bacteremia in Mice," Plos One, Mar. 1, 2013, vol. 8, No. 3.

Chia-Te Kung et al., "Serum adhesion molecules as predictors of bacteremia in adult severe sepsis patients at the emergency department," Clinica Chimica Acta, Jun. 1, 2013, pp. 116-120, vol. 421.

Danfeng Xu et al., "Brain-derived neurotrophic factor is regulated via MyD88/NF-[kappa]B signaling in experimental *Streptococcus pneumoniae* meningitis," Scientific Reports, Jun. 14, 2017, vol. 7, No. 1.

Jinwu Chen et al., "Coagulation factors VII, IX and X are effective antibacterial proteins against drug-resistant Gram-negative bacteria," Cell Research, Aug. 9, 2019, pp. 711-724, vol. 29, No. 9.

Markus Bosmann et al., "Therapeutic potential of targeting IL-17 and IL-23 in sepsis," Clinical and Translational Medicine, Apr. 27, 2012, vol. 1, No. 1.

R. P. Dellinger et al., "Surviving Sepsis Campaign: International Guidelines for Management of Severe Sepsis and Septic Shock, 2012," Intensive Care Med, Jan. 30, 2013, pp. 165-228, vol. 39.

Bryan Coburn, MD, PHD et al., "Does This Adult Patient With Suspected Bacteremia Require Blood Cultures?," JAMA, Aug. 1, 2012, pp. 502-511, vol. 308, No. 5.

Benjamin M P Tang et al., "Accuracy of procalcitonin for sepsis diagnosis in critically ill patients: systematic review and meta-analysis," Lancet Infect Dis., Mar. 2007, pp. 210-217, vol. 7.

Bernard Uzzan, MD et al., "Procalcitonin as a diagnostic test for sepsis in critically ill adults and after surgery or trauma: A systematic review and meta-analysis," Crit Care Med, Jul. 2006, pp. 1,996-2,003, vol. 37, No. 7.

C. Cheval et al., "Procalcitonin (PCT) is useful in predicting the bacterial origin of an acute circulatory failure in critically ill patients," Intensive Care Med, Mar. 2000, pp. S153-S158, 26 Suppl 2.

Ugarte, Hector MD et al., "Procalcitonin used as a marker of infection in the intensive care unit," Crit Care Med, Mar. 1999, pp. 498-504, vol. 27.

Virginia L. Vega PHD, "A marker for posttraumatic-sepsis: Searching for the Holy Grail around intensive care units," Crit Care Med, May 2009, pp. 1,806-1,807, vol. 37, No. 5.

Daniel Kirchhofer et al., "Active Site-Blocked Factors VIIa and IXa Differentially Inhibit Fibrin Formation in a Human Ex Vivo Thrombosis Model," Aug. 1995, pp. 1,098-1,106, vol. 15, No. 8.

Daniel Kirchhofer et al., "Endothelial Cells Stimulated with Tumor Necrosis Factor-a Express Varying Amounts of Tissue Factor Resulting in Inhomogenous Fibrin Deposition in a Native Blood Flow System: Effects of Thrombin Inhibitors," J. Clin. Invest., May 1994, pp. 2,073-2,083, vol. 93.

Ian Sabroe et al., "Toll-Like Receptors in Health and Disease: Complex Questions Remain," The Journal of Immunology, Aug. 15, 2003, pp. 1,630-1,635, vol. 171, No. 4.

Yanxian Feng et al., "A toll-like receptor agonist mimicking microbial signal to generate tumor-suppressive macrophages," Nature Communications, May 22, 2019.

Jayesh M. Bhatt, "Treatment of pulmonary exacerbations in cystic fibrosis," European Respiratory Review 2013, Sep. 2013, pp. 205-216, vol. 22.

Valerie Waters et al., "Pulmonary Exacerbations in Children with Cystic Fibrosis," Ann Am Thorac Soc., Nov. 2015.

Henry J. Fuchs, M.D., "Effect of Aerosolized Recombinant Human DNase on Exacerbations of Respiratory Symptoms and on Pulmonary Function in Patients with Cystic Fibrosis," N Engl J Med, Sep. 1994, pp. 637-642, vol. 331, No. 10.

Miriam M. Treggiari et al., "Early anti-pseudomonal acquisition in young patients with cystic fibrosis: rationale and design of the EPIC clinical trial and observational study," Contemp Clin Trials, May 2009, pp. 256-268, vol. 30, No. 3.

Joachim E. Fischer et ai., "A readers' guide to the interpretation of diagnostic test properties: clinical example of sepsis," Intensive Care Med, May 7, 2003, pp. 1,043-1,051, vol. 29.

John C. Woodfield et al., "Incidence and significance of postoperative complications occurring between discharge and thirty days: a prospective cohort study," Journal of Surgical Research, Jun. 2016.

Office action dated Feb. 20, 2026, in Columbian application No. NC2022/0017616.

Mirrin J. Dorresteijn et al., Lipopolysaccharide-stimulated whole blood cytokine production does not predict the inflammatory response in human endotoxemia. Innate Immunity. 2010; 16(4): 248-253. doi: 10.1177/1753425909339923.

* cited by examiner

METHOD AND KIT FOR THE EARLY DETECTION OF SEPSIS

FIELD OF THE INVENTION

The present invention relates to methods and kits for diagnosis of sepsis. In particular, the invention relates to the use of biomarkers for the diagnosis and treatment of sepsis.

BACKGROUND OF INVENTION

Sepsis, a syndrome of systemic inflammation in response to infection, kills approximately 750,000 people in the United States every year. It is also the single most expensive condition treated in the US, costing the healthcare system more than $24 billion annually. Prompt diagnosis and treatment of sepsis is crucial to reducing mortality, with every hour of delay increasing mortality risk. Sepsis is defined by the presence of systemic inflammatory response syndrome (SIRS), in addition to a known or suspected source of infection (Dellinger et al. (2013) Intensive Care Med 39: 165-228). However, SIRS is not specific for sepsis, as sterile inflammation can arise as a nonspecific response to trauma, surgery, thrombosis, and other non-infectious insults. Thus, sepsis can be difficult to distinguish clinically from systemic inflammation caused by non-infectious sources, such as tissue trauma (Coburn et al. JAMA (2012) 308:502-511). There is no 'gold standard' blood test for distinguishing patients with infections at time of diagnosis, before results become available from standard microbiological cultures. One of the most common biomarkers of infection, procalcitonin, has a summary area under the receiver operating characteristic curve (AUC) of 0.78 (range 0.66-0.90) (Tang et al. (2007) Lancet Infect Dis 7:210-217; Uzzan et al. (2006) Crit Care Med 34: 1996-2003; Cheval et al. (2000) Intensive Care Med 26 Suppl 2:S153-158; Ugarte et al. (1999) Crit Care Med 27:498-504). Several groups have evaluated whether cytokine or gene expression arrays can accurately diagnose sepsis; however, due to the highly variable nature of host response and human genetics, no robust diagnostic signature has been found. Indeed, "finding the 'perfect' sepsis marker has been one of the most elusive dreams in modern medicine" (Vega et al. (2009) Crit Care Med 37: 1806-1807).

Taking into account the heterogeneity of septic patients therefore becomes more and more vital when selecting a homogeneous population during clinical trials but also during the implementation of therapies which are more and more personalized. This is all the more important since certain proposed therapies generate totally opposite effects on the immune response, and can therefore be harmful to the patients if they do not present the immuno-inflammatory status suitable for the therapeutic choice. It is therefore important to have a process and a kit which make it possible to reliably establish the overall immune status of the patient when he enters an accident and emergency or intensive care unit, and which also make it possible to define the level of deregulation of each of the components of the immuno-inflammatory response in order to implement the best-targeted therapy according to the established immune response (innate and/or adaptive). There remains a need for sensitive and specific diagnostic tests for sepsis that can distinguish patients that have bloodstream infection than not, such as caused by traumatic injury and SIRS

SUMMARY OF THE INVENTION

The authors of the invention have found that septic patients display a characteristic biomarker profile when exposed to endotoxins, which allows the detection of infectious agents in the bloodstream. This specific marker profile is suitable for the prediction of the microbiologic blood culture outcome and therefore, makes possible an early diagnosis of the disease. These biomarkers could be used alone or in combination with one or more additional biomarkers or relevant clinical parameters in prognosis, monitoring or treatment of sepsis. In this regard, as it is shown in the examples 1 and 2 of the present application, the TNF-α and IL-1β expression levels in whole blood from samples of subjects suffering from bacteremia after LPS challenge were lower than the expression levels of said cytokines in control subjects; and the IL-10 and CCL2 expression levels in whole blood after LPS challenge were higher that the expression level of said cytokines in control subjects. Thus, these results demonstrate that the expression levels of certain cytokines present in a blood sample suffer a variation upon the exposure of the sample to a TLR-4 agonist such as LPS and this variation can be utilized for the diagnosis of the presence of bacteremia in a short period of time.

Thus, in a first aspect, the invention relates to an in vitro method for detecting bacteremia in a subject comprising:

(a) contacting a blood sample from the subject with a TLR4 agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and
(c) comparing said level with a reference value, wherein
  a decreased level of TNFα, IL-1b and/or IFN-β compared to the reference value and/or
  an increased level of IL-10, CCL2, IL-2, IL-4 and/or VEGF compared to the reference value is indicative of the presence of bacteremia in the blood from the subject.

In a second aspect the invention relates to an in vitro method for selecting a therapy for a subject suffering from systemic inflammatory response syndrome (SIRS), comprising:

(a) contacting a blood sample from the subject with a TLR4 agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and
(c) comparing said expression level with a reference value, wherein if
  a decreased level of TNFα, IL-1b and/or IFN-β compared to the reference value and/or
  an increased level of IL-10, CCL2, IL-2, IL-4 and/or VEGF compared to the reference value is detected, a therapy with one or more broad spectrum antibiotics is selected.

In a third aspect, the invention relates to an in vitro method for selecting a therapy for a subject suffering from cystic fibrosis, comprising:

(a) contacting a blood sample from the subject with a TLR4 agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF and in the blood sample previously contacted with the TLR4 agonist and (c) comparing said expression level with a reference value, wherein if a decreased level of TNFα, IL-1b and/or IFN-β compared to the reference value and/or an increased level of IL-10, CCL2, IL-2, IL-4 and/or VEGF compared to the reference value is detected, then if the subject is not under treatment with an antibiotic, then a therapy with one or more broad spectrum antibiotics is selected, and if the subject is under treatment with an antibiotic, said antibiotic is replaced by a different type of antibiotic or the dosage of said antibiotic is changed.

In a fourth aspect, the invention relates to an in vitro method for selecting a subject suffering from systemic inflammatory response syndrome (SIRS) for a therapy with one or more broad spectrum antibiotics, comprising:

(a) contacting a blood sample from the subject with a TLR4 agonist in the presence of an anticoagulant, (b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and (c) comparing said expression level with a reference value, wherein the subject is selected for said therapy if a decreased level of TNFα, IL-1b and/or IFN-β compared to the reference value and/or an increased level of IL-10, CCL2, IL-2, IL-4 and/or VEGF compared to the reference value is detected.

In a fifth aspect, the invention relates to an in vitro method for selecting a subject suffering from cystic fibrosis who is not under treatment with an antibiotic for a therapy with one or more broad spectrum antibiotics, or for selecting a subject suffering from cystic fibrosis who is under treatment with an antibiotic for a therapy with a different type of antibiotic or for a therapy with a different dosage of said antibiotic, comprising:

(a) contacting a blood sample from the subject with a TLR4 agonist in the presence of an anticoagulant, (b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and (c) comparing said expression level with a reference value, wherein the subject is selected for said therapy if a decreased level of TNFα, IL-1b and/or IFN-β compared to the reference value and/or an increased level of IL-10, CCL2, IL-2, IL-4 and/or VEGF compared to the reference value is detected.

In a sixth aspect, the invention relates to a kit comprising a reagent specific for determining the level of at least one gene selected from the group consisting of tumor necrosis factor alpha (TNFα), IL-1b, IL-10, CCL2, interferon beta (IFN-β), IL-17, IL-2, IL-4 and VEGF.

Additionally, in a seventh aspect, the invention relates to the use of the kit of the sixth aspect of the invention for detecting bacteremia in a subject, diagnosing sepsis in a subject suffering from systemic inflammatory response syndrome and/or detecting bacterial pulmonary exacerbation in a subject suffering from cystic fibrosis.

Finally, in an eighth aspect, the invention relates to a method for the preparation and reading of a blood sample by a reader, by means of the kit of the sixth aspect of the invention.

DETAILED DESCRIPTION OF THE INVENTION

Figure 1:
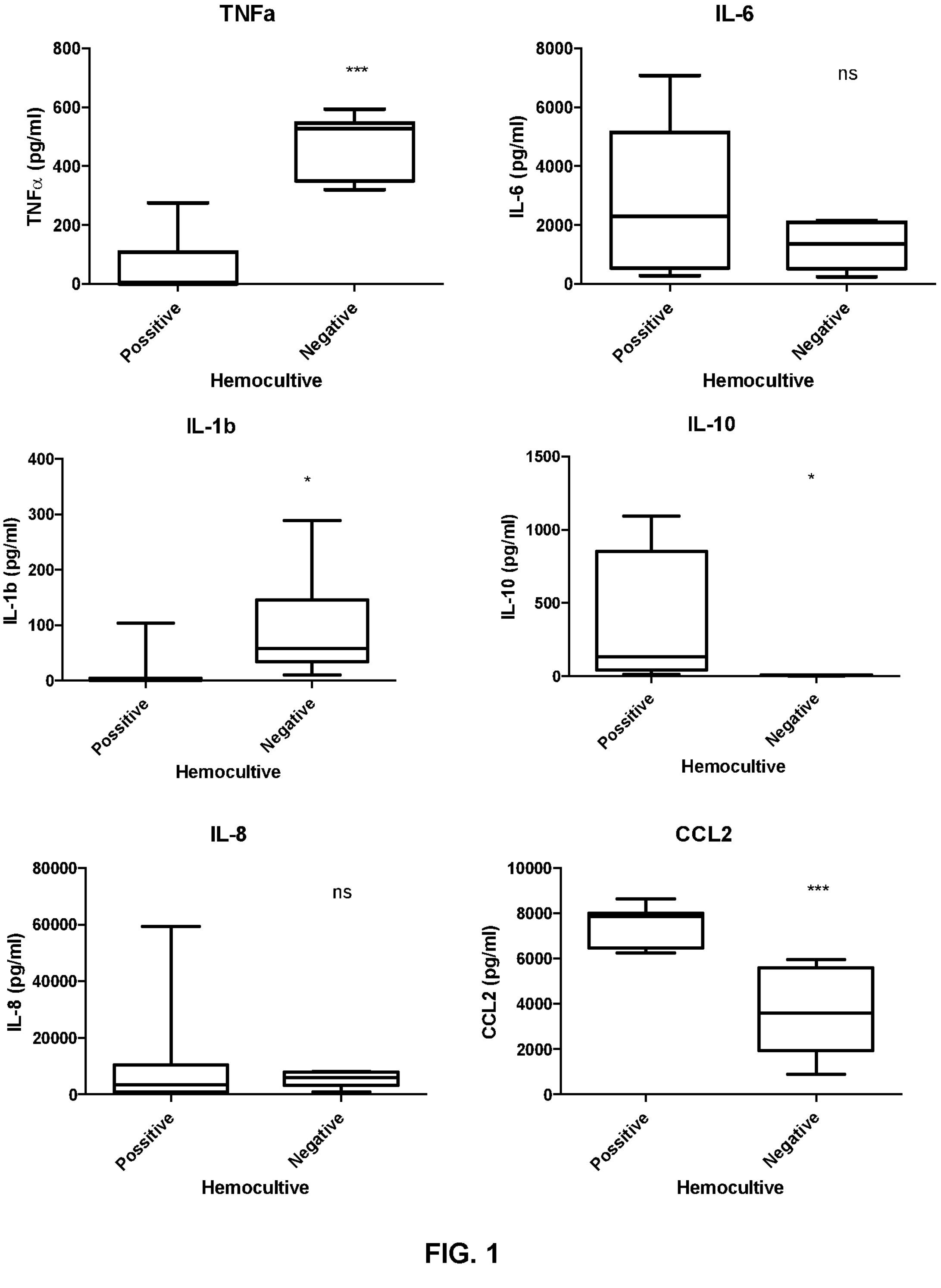
FIG. 1. Quantification of biomarkers after LPS challenge. TNFα, IL-1μ, IL-6, IL-8, CCL-2, IL-10, serum PCR and procalcitonine whole-blood production after ex vivo *B. abortus* LPS stimulation (5 ng/mL, 2 h) were quantified by cytometric bead array (n=25). ***, p<0.005; *, p<0.05 compare blood culture positive patients vs blood culture negative patients using unpaired t-test.
Figure 1:
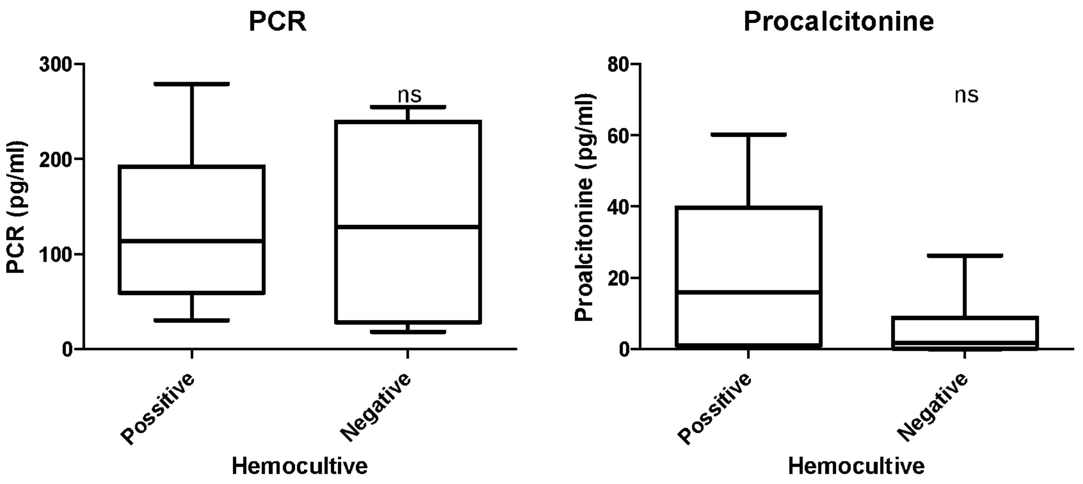

The authors of the invention have developed a methodology for early diagnosis of sepsis based on the variation of the expression level of specific cytokines of blood samples of septic patients when exposed to LPS with regard to the variation observed in control subjects. This specific diagnostic test will allow the identification of septic patients among the subjects suffering from SIRS and therefore to take the necessary therapeutic decisions in order to overcome the disease in an early stage.

With regard to the terms used in the present description, unless otherwise defined, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

Method for Detecting Bacteremia

In a first aspect, the invention relates to an in vitro method, hereinafter first method of the invention, for detecting bacteremia in a subject comprising:

(a) contacting a blood sample from the subject with TLR4 receptor agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the endotoxin and
(c) comparing said level with a reference value, wherein a decreased level of TNFα, IL-1b and/or IFN-β compared to the reference value and/or
an increased level of IL-10, CCL2, IL-2, IL-4 and/or VEGF compared to the reference value is indicative of the presence of bacteremia in the subject.

The term "in vitro", as used herein, refers to the fact that the method is not carried out on the body of a human or animal subject, but rather on cells or fluids isolated from said subject or in a test tube.

As used herein the term "detecting" and derivations of this term refer to determining the presence, absence or amount of a biomarker in a sample. According to the present invention, "detecting" also includes determining, evaluating, quantifying, or measuring. This term also includes detecting the selected gene at a time point and detecting the same gene over time (also denoted herein as "monitoring" and derivations of this term).

As used herein, the term "bacteremia" refers to the presence of bacteria that are alive and capable of reproducing in the bloodstream. It is a type of bloodstream infection. Bacteremia can be either a primary or secondary process. In primary bacteremia, bacteria have been directly introduced into the bloodstream. Injection drug use may lead to primary bacteremia. In the hospital setting, use of blood vessel catheters contaminated with bacteria may also lead to primary bacteremia. Secondary bacteremia occurs when bacteria have entered the body at another site, such as the cuts in the skin, or the mucous membranes of the lungs (respiratory tract), mouth or intestines (gastrointestinal tract), bladder (urinary tract), or genitals. Bacteria that have infected the body at these sites may then spread into the lymphatic system and gain access to the bloodstream, where further spread can occur.

Bacteremia may also be defined by the timing of bacteria presence in the bloodstream: transient, intermittent, or persistent. In transient bacteremia, bacteria are present in the bloodstream for minutes to a few hours before being cleared from the body, and the result is typically harmless in healthy people. This can occur after manipulation of parts of the body normally colonized by bacteria, such as the mucosal surfaces of the mouth during teeth brushing, flossing, or dental procedures, or instrumentation of the bladder or colon. Intermittent bacteremia is characterized by periodic seeding of the same bacteria into the bloodstream by an existing infection elsewhere in the body, such as an abscess, pneumonia, or bone infection, followed by clearing of that bacteria from the bloodstream. This cycle will often repeat until the existing infection is successfully treated. Persistent bacteremia is characterized by the continuous presence of bacteria in the bloodstream. It is usually the result of an infected heart valve, a central line-associated bloodstream infection (CLABSI), an infected blood clot (suppurative thrombophlebitis), or an infected blood vessel graft. Persistent bacteremia can also occur as part of the infection process of typhoid fever, brucellosis, and bacterial meningitis. Left untreated, conditions causing persistent bacteremia can be potentially fatal.

Bacteremia can be caused by gram-positive or gram-negative bacteria. Therefore, in a particular embodiment, bacteremia is caused by any of gram-positive or gram-negative bacteria. In another embodiment, the bacteremia is caused by gram-positive bacteria. In another particular embodiment, the bacteremia is caused by gram-negative bacteria.

The meaning of the terms gram-positive and gram-negative bacteria are readily apparent and understood by a person skilled in art, as well as the technology for the differentiation and identification of the bacterium responsible of the bacteremia.

Gram-positive bacteria are bacteria with thick cell walls. In a Gram stain test, these organisms yield a positive result. The test, which involves a chemical dye, stains the bacterium's cell wall purple. The hallmark trait of gram-positive bacteria is their structure. Generally, they have the following characteristics:

No outer membrane. Gram-positive bacteria do not have an outer membrane, but gram-negative bacteria do.

Complex cell wall. The cell wall, which surrounds the cytoplasmic membrane, consists of peptidoglycan, polysaccharides, teichoic acids, and proteins. It can easily absorb foreign material.

Thick peptidoglycan layer. In gram-positive bacteria, the peptidoglycan is 40 to 80 layers thick.

Certain surface appendages. Gram-positive bacteria may have flagella, which help them move. They rarely have hair-like structures called pili.

Regarding gram-positive bacteria, *Staphylococcus, Streptococcus*, and *Enterococcus* species are the most important and most common species that can enter the bloodstream. These bacteria are normally found on the skin or in the gastrointestinal tract.

*Staphylococcus aureus* is the most common cause of healthcare-associated bacteremia and is also an important cause of community-acquired bacteremia. Skin ulceration or wounds, respiratory tract infections, and IV drug use are the most important causes of community-acquired *S aureus* bacteremia. In healthcare settings, intravenous catheters, urinary tract catheters, and surgical procedures are the most common causes of staph aureus bacteremia.

There are many different types of streptococcal species that can cause bacteremia. Group A *Streptococcus* (GAS) typically causes bacteremia from skin and soft tissue infections. Group B *Streptococcus* is an important cause of bacteremia in neonates, often immediately following birth. Viridans streptococci species are normal bacterial flora of the mouth. Viridans strep can cause temporary bacteremia after eating, tooth brushing, or flossing. More severe bacteremia can occur following dental procedures or in patients receiving chemotherapy. Finally, *Streptococcus bovis* is a common cause of bacteremia in patients with colon cancer.

Enterococci are an important cause of healthcare-associated bacteremia. These bacteria commonly live in the gastrointestinal tract and female genital tract. Intravenous catheters, urinary tract infections and surgical wounds are all risk factors for developing bacteremia from enterococcal species. Resistant enterococcal species can cause bacteremia in patients who have had long hospital stays or frequent antibiotic use in the past.

Other non-limiting examples of gram-positive bacterial species that can cause bacteremia are *Streptococcus pneumoniae, Streptococcus pyrogenes, Staphylococcus aureus, Staphylococcus epidermidis, Streptococcus agalactiae, Enterococcus* spp, *Clostridium tetani, Clostridium botulinum, Clostridium perfringens, Clostridium difficile, Cacillus anthracis, Corynebacterium diphtheria* and *Listeria monocytogenes, Bacillus subtilis, Enterococcus faecalis, Enterococcus faecium, Mycoplasma pneumophila, Streptococcus pneumoniae, Staphylococcus cohnii, Staphylococcus condiment, Staphylococcus gallinarum, Staphylococcus haemolyticus, Staphylococcus hominis, Staphylococcus intermedius, Staphylococcus lentus, Staphylococcus lugdunensis, Staphylococcus piscifermentans, Staphylococcus xylosus, Streptococcus agalactiae, Streptococcus bovis, Streptococcus canis, Streptococcus dysgalactiae, Streptococcus equi, Streptococcus equinus, Streptococcus gordonii, Streptococcus hyointestinalis, Streptococcus intermedius, Streptococcus milleri, Streptococcus mitis, Streptococcus oralis, Streptococcus porcinus, Streptococcus pyogenes, Streptococcus salivarius, Streptococcus sanguinis, Streptococcus suis, Streptococcus uberis, Bacillus anthracis, Bacillus cereus, Bacillus coagulans, Listeria monocytogenes, Clostridium perfringens, Clostridium botulinum, Staphylococcus schleiferi, Staphylococcus saprophyticus, Micrococcus luteus, Rothia mucilaginosa, Weissella confusa, Lactobacillus casei, Enterococcus casseliflavus, Aerococcus urinae, Aerococcus viridans, Listeria grayi, Corynebacterium diphtheria, Corynebactenium jeikeium* and *Corynebacterium* Group B Gram-negative bacteria are bacteria that do not retain the crystal violet stain used in the Gram staining method of bacterial differentiation. They are characterized by their cell envelopes, which are composed of a thin peptidoglycan cell wall sandwiched between an inner cytoplasmic cell membrane and a bacterial outer membrane.

Typically, gram-negative organisms have the following traits:

- outer lipid membrane
- thin peptidoglycan layer (2 to 3 nanometers)
- usually doesn't have teichoic acids
- can have flagella or pili Gram-negative bacterial species are responsible for approximately 24% of all cases of healthcare-associated bacteremia and 45% of all cases of community-acquired bacteremia. In general, Gram-negative bacteria enter the bloodstream from infections in the respiratory tract, genitourinary tract, gastrointestinal tract, or hepatobiliary system. Gram-negative bacteremia occurs more frequently in elderly populations (65 years or older) and is associated with higher morbidity and mortality in this population.

*E. coli* is the most common cause of gram-negative community-acquired bacteremia accounting for approximately 75% of cases. *E. coli* bacteremia is usually the result of a urinary tract infection. Other gram-negative organisms that can cause community-acquired bacteremia include without limitation *Pseudomonas aeruginosa, Klebsiella pneumoniae* and *Proteus mirabilis.*

*Pseudomonas* and *Enterobacter* species are the most important causes of gram negative bacteremia in the ICU.

Other possible gram-negative bacteria causing bacteremia include without limitation *Klebsiella* spp., *Klebsiella pneumoniae, Proteus* spp., *Bacteroides fragilis, Pseudomonas aeruginosa, Acinetobacter baumannii*, and *Salmonella* spp., *Salmonella typhimurium, Providencia alcalifaciens, Providencia rettgeri, Burkholderia cepaci, Yersinia kristensenii, Yersinia enterocolitica, Citrobacter amalonaticus, Citrobacter, Proteus mirabilis, Proteus vulgaris, Enterobacter sakazakii, Brevundimonas diminuta, Acinetobacter anitratus, Haemophilus parainfluenzae, Haemophilus paraphrophilus, Neisseria meningitidis, Neisseria gonorrhoeae, Neisseria mucosa, Neisseria lactamica, Neisseria cinerea, Bacteroides thetaiotaomicron, Bacteroides ovatus, Bacteroides fragilis, Afipia felis, Vibrio cholerae, Eikenella corrodens, Pasteurella multocida, Campylobacter jejuni, Serratia liquefaciens, Serratia odorifera, Acinetobacter baumannii, Acinetobacter calcoaceticus, Acinetobacter lwoffi, Bordetella pertussis, Bordetella ansorpii, Bordetella, Bordetella avium, Chlamydophila pneumoniae, Citrobacter freundii, Enterobacter aerogenes, Enterobacter cloacae, Haemophilus influenzae, Haemophilus aphrophilus, Klebsiella pneumoniae, Klebsiella oxytoca, Legionella pneumophila, Moraxella catarrhalis, Morganella morganii, Moraxella nonliquefaciens, Pseudomonas aeruginosa, Proteus mirabilis, Proteus vulgaris, Pseudomonas fluorescens, Pseudomonas putida, Pseudomonas stutzeri, Salmonella typhimurium, Salmonella typhi, Shigella flexneri, Shigella sonnei, Neisseria gonorrhoeae, Neisseria meningitidis, Helicobacter pylori, Salmonella enteritidis, Serratia marcescens, Empedobacter brevis, Stenotrophomonas maltophilia.*

Bacteremia is clinically distinct from sepsis, which is a condition where the blood stream infection is associated with an inflammatory response from the body, often causing abnormalities in body temperature, heart rate, breathing rate, blood pressure, and white blood cell count.

The term "subject" or "patient" typically includes humans, but can also include other animals such as, e.g., other primates, rodents, canines, felines, equines, ovines, porcines, and the like. In a preferred embodiment, the subject is a male or female human subject of any race or age. The term "blood sample" refers to whole blood sample or plasma. In a particular embodiment, the blood sample is "whole blood sample". The term, "whole blood sample", as understood in the invention, is a blood sample already obtained (i.e., previously extracted from a subject, preferably a human subject) which has not been treated to remove insoluble components from blood. A whole blood sample, therefore contains insoluble components. A serum sample or a plasma sample is not comprised in the term "whole blood sample". Preferably, the whole blood sample is a peripheral blood sample because it is easier to obtain.

Blood is made up of an acellular fraction (blood plasma) and various cellular fractions (such as for example red blood cells, leukocytes) and platelet elements, which can be used in the scope of the present invention as the blood sample to be analysed.

A blood plasma fraction sample can also be used for carrying out the aforementioned method of analysis. Therefore, in another embodiment, the blood sample is plasma.

As it is understood in the invention, "plasma" refers to the liquid element of blood, representing 60% of the total blood volume and lacking red and white blood cells. The plasma fraction is preferred over the platelet fraction because it is easier to obtain, besides the fact that the difficulties in obtaining platelets due to platelet aggregation or rupture phenomena are well-known.

The present invention can be carried out on substantially platelet-free plasma.

The various methods of collecting blood samples consist of obtaining blood in tubes with anticoagulant and subjecting them to different centrifugation conditions according to the different protocols, such that the blood separates into its basic components depending on density, selecting that fraction corresponding to the platelet-rich plasma. Commercial kits such as RegenPRP-Kit (RegenLab) can alternatively be used.

According to the invention, the blood plasma fraction to be analysed can be obtained previously from a blood sample (preferably peripheral blood) already obtained by means of any of the standard blood fractionation processes, such as centrifugation-filtration fractionation for example.

The blood sample is typically extracted by means of puncturing an artery or vein, normally a vein from the inner part of the elbow or from the back of the hand, the blood sample being collected in an air-tight vial or syringe. A capillary puncture normally on the heel or on the distal phalanxes of fingers can be performed for analysis by means of a micromethod. To obtain the plasma sample the complete blood is contacted with an anticoagulant and is centrifuged at 3,000 rpm for 20 minutes. The precipitate of said centrifugation corresponds to the formed elements, and the supernatant corresponds to the plasma. The whole blood or plasma obtained can be transferred to a storage tube for sample analysis by means of the method of the invention.

The step of contacting the blood sample with a TLR4 inhibitor is carried out in the presence of an anticoagulant. The term "anticoagulant", as used herein, refers to a substance that can prevent, inhibit or prolong blood coagulation in an in vitro or in vivo assay of blood coagulation. Blood coagulation assays are known in the art and include, for example, prothrombin time assays, the human ex vivo thrombosis model described by Kirchhofer et al., Arterioscler. Thromb. Vasc. Biol. 15: 1098-1106 (1995); and Kirchhofer et al., J. Clin. Invest. 93: 2073-83 (1994), and assays based on the measurement of Factor X activation in human plasma. Illustrative non-limitative examples of anticoagulants include EDTA, sodium citrate, heparin, lithium heparin, sodium fluoride, sodium oxalate, blood preservatives, such as CPD comprising sodium citrate, citric acid, glucose and sodium dihydrogen phosphate, or the like. In a particular embodiment, the blood sample is prepared by adding, to a collected blood, an anticoagulant, in which case the step of contacting the blood sample with the TLR4 agonist can be performed by adding the TRL-4 agonist to the blood sample which is already mixed with the anticoagulant.

In a particular embodiment, the anticoagulant is lithium heparin.

In a particular embodiment, within the context of the method of the invention, after step (a) the blood sample is separated into cells and plasma, the determination of the expression level of the at least one gene is carried out by determining the levels of the mRNA of said gene in the cells and/or by determining the levels of the protein encoded by said gene in the plasma.

The term "contacting", as used herein refers to the process by which the blood sample comes into contact with the TLR4 agonist and includes any possible method that allows the interaction of the blood sample with the TLR4 agonist. Thus, upon the mixing of the blood sample and the TLR4 agonist, a characteristic biomarker pattern is displayed when there is bacteremia in the subject.

In a particular embodiment, the process of contacting the blood sample with the TLR4 agonist takes place for between 15 minutes and 4 hours, more preferably, for between 30 minutes and 3 hours, and more preferably for between 1 hour and 2 hours.

In a particular embodiment, the determination of the expression level of the at least one gene is performed after the blood sample is contacted with the TLR4 agonist for a period of time between 1 and 3 hours.

In another particular embodiment, the temperature at which the process of contacting the blood sample with the TLR4 agonist takes place is between 150 and 40° C., more preferably, between 20° and 40° C., and more preferably, between 30° and 40° C. Any combinations of time and temperature as the ones specified herein are suitable for the contacting step of the method of the invention.

By "TLR4 agonist" it is meant a compound which is capable of causing a signalling response through the Toll-like receptor 4 (TLR4) signalling pathway, either as a direct ligand (directly binding to TLR4) or indirectly through the generation of an endogenous or exogenous ligand of TLR4 (Sabroe et al, JI 2003 p 1630-5). The term "Toll-like receptor 4" or "TLR4" refers to a transmbembrane protein, which in humans is encoded by the TLR4 gene, member of the Toll-like receptor family. Its activation leads to an intracellular signalling pathway NF-κβ and inflammatory cytokine production. In a particular embodiment, the TLR4 is the human TLR4. In a particular embodiment, the TRL4 is the protein with the sequence identified by the UniProtKB/Swiss-Prot accession number O00206 (Entry version 208, 11 Dec. 2019, Sequence version 2, 1 Jan. 1998). Suitable examples of a TLR4 agonist include endotoxins, such as lipopolysaccharide (LPS), bacterial HSP60, mannunoric acid polymers, flavolipins, teichuronic acids, *S. pneumoniae* pneumolysin, bacterial fimbriae, respiratory syncytial virus coat protein, surfactant protein A, hyaluronan oligosaccharides, heparin sulphate fragments, fibrinogen peptides and β-defensin-2.

The ability of a particular substance of activating TLR4, so that the substance can be considered a TLR4 agonist, can be determined by any assay directed to evaluate TLR4 activation. TLR4 cooperates with MD-2 (also called LY96) and CD14 to mediate signal transduction events induced by LPS. LPS recognition by TLR4 can trigger two different signalling pathways: a MyD88 dependent pathway that results in NF-κβ release, and MyD88 dependent pathway, resulting in the production of type 1 interferons. Thus, the ability of a substance to activate TL4R downstream signalling can be evaluated by means of an assay directed to measure NF-κβ translocation by microscopy, NF-κβ binding to a promoter-reporter by SEAP or luciferase expression, up-regulation of an NF-κβ-regulated gene such as IL-1beta, or degradation of a negative inhibitor of NF-κβ such as IkBalpha by western blot, or by quantifying the level of secreted embryonic alkaline phosphatase as disclosed by Feng Y et al., (Nat Commun. 2019 May 22; 10(1):2272).

In a particular embodiment, the TLR4 agonist is an endotoxin. The term "endotoxin" or "endotoxins" includes or means or may be used interchangeably with the term "lipopolysaccharide" or "LPS". The term "lipopolysaccharide" or "LPS" refers to a major constituent of the outer-leaflet of the membranes of Gram-negative bacteria and consists of the following three distinct domains: 1) the 0-antigen region, which is a strain-specific polysaccharide moiety and determines the antigenic specificity of the organism; 2) the core region, which is relatively conserved with respect to its sugar composition and may play a role in maintaining the integrity of the outer membrane; and 3) the lipid A region, which is also conserved and functions as a hydrophobic anchor holding lipopolysaccharide in place. The lipid A portion of lipopolysaccharide constitutes most of the outer monolayer of the outer membrane in Gram-negatives. Examples of LPS Gram-negative producing bacteria include without limitation *Escherichia coli, Salmonella, Shigella, Pseudomonas, Neisseria, Haemophilus influenzae, Bordetella pertussis* and *Vibrio cholera*. In a particular embodiment, the LPS is produced by *E. coli*. In another particular embodiment, the LPS is produced by *Brucella abortus*.

The term "LPS" includes suitable non-toxic derivatives of lipid A, particularly monophosphoryl lipid A or more particularly 3-Deacylated monophoshoryl lipid A (3D-MPL).

3D-MPL is sold under the name MPL by GlaxoSmithKline Biologicals N.A. and is referred as MPL or 3D-MPL, see, for example, U.S. Pat. Nos. 4,436,727; 4,877,611; 4,866,034 and 4,912,094. 3D-MPL primarily promotes CD4+ T cell responses with an IFN-g (Th1) phenotype. Chemically it is a mixture of 3-deacylated monophosphoryl lipid A with 4, 5 or 6 acylated chains.

In an embodiment, the first method of the invention allows detecting bacteremia caused by an endotoxin. Therefore, in this particular embodiment, this method can be also referred to as a method for detecting the presence of endotoxin in the blood of a subject.

Other TLR4 agonists which can be used are alkyl Glucosaminide phosphates (AGPs) such as those disclosed in WO98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840.

Other suitable TLR4 agonists are as described in WO2003/011223 and in WO 2003/099195, such as compound I, compound II and compound III disclosed on pages 4-5 of WO2003/011223 or on pages 3 to 4 of WO2003/099195 and in particular those compounds disclosed in WO2003/011223 as ER803022, ER803058, ER803732, ER804053, ER804057m ER804058, ER804059, ER804442, ER804680 and ER804764. For example, one suitable TLR4 agonist is ER804057.

In an embodiment, the TLR4 agonist is not an endotoxin.

In another embodiment, the TLR4 agonist is a non-naturally occurring agonist.

"Non-naturally-occurring" means an agent that it is not found in nature as such, that is, that is does not exist in nature. Non limiting examples of non-naturally-occurring agonists include without limitation compound I, compound II and compound III disclosed on pages 4-5 of WO2003/011223 or on pages 3 to 4 of WO2003/099195 and in particular those compounds disclosed in WO2003/011223 as ER803022, ER803058, ER803732, ER804053, ER804057m ER804058, ER804059, ER804442, ER804680 and ER804764. For example, one suitable TLR4 agonist is ER804057.

The second step of the first method of the invention comprises determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR-4 agonist.

The term "expression level", as used herein, refers to a measurable quantity of a gene product produced by the gene in a sample of the subject, wherein the gene product can be a transcriptional product or a translational product. As understood by the person skilled in the art, the gene expression level can be quantified by measuring the messenger RNA levels of said gene or of the protein encoded by said gene.

In a particular embodiment, the expression level of said gene is determined by measuring the messenger RNA (mRNA) levels of said gene or the levels of the protein encoded by said gene.

The level of a messenger RNA can be determined by methods well known in the art. For example, the nucleic acid contained in the blood sample is first extracted according to standard methods, for example using lytic enzymes or chemical solutions or extracted by nucleic-acid-binding resins following the manufacturer's instructions. The extracted mRNA is then detected by hybridization (e.g., Northern blot analysis or by oligonucleotide microarrays after converting the mRNA into a labelled cDNA) and/or amplification (e.g., RT-PCR). Quantitative or semi-quantitative RT-PCR is preferred. Real-time quantitative or semi-quantitative RT-PCR is particularly advantageous. Preferably, primer pairs can be designed in order to overlap an intron, to distinguish cDNA amplification from putative genomic contamination. Suitable primers may be easily designed by the skilled person. Other methods of amplification include ligase chain reaction (LCR), transcription-mediated amplification (TMA), strand displacement amplification (SDA) and nucleic acid sequence based amplification (NASBA). Preferably, the quantity of mRNA is measured by quantitative or semi-quantitative RT-PCR or by real-time quantitative or semi-quantitative RT-PCR.

The level of a protein can be determined by any method known in the art suitable for the determination and quantification of a protein in a sample. By way of a non-limiting illustration, the level of a protein can be determined by means of a technique which comprises the use of antibodies with the capacity for binding specifically to the assayed protein (or to fragments thereof containing the antigenic determinants) and subsequent quantification of the resulting antigen-antibody complexes, or alternatively by means of a technique which does not comprise the use of antibodies such as, for example, by techniques based on mass spectroscopy. The antibodies can be monoclonal, polyclonal or fragment thereof, Fv, Fab, Fab' and F(ab')2, scFv, diabodies, triabodies, tetrabodies and humanized antibodies. Similarly, the antibodies may be labelled. Illustrative, but non-exclusive, examples of markers that can be herein used include radioactive isotopes, enzymes, fluorophores, chemiluminescent reagents, enzyme cofactors or substrates, enzyme inhibitors, particles, or dyes. There is a wide variety of known tests that can be used according to the present invention, such as combined application of non-labelled antibodies (primary antibodies) and labelled antibodies (secondary antibodies), Western blot or immunoblot, ELISA (enzyme-linked immunosorbent assay), RIA (radioimmunoassay), competitive EIA (enzyme immunoassay), DAS-ELISA (double antibody sandwich ELISA), two-dimensional gel electrophoresis, capillary electrophoresis, immunocytochemical and immunohistochemical techniques, immunoturbidimetry, immunofluorescence, techniques based on the use of biochips or protein microarrays including specific antibodies or assays based on the colloidal precipitation in formats such as reagent strips and assays based on antibody-linked quantum dots. Other forms of detecting and quantifying proteins include, for instance, affinity chromatography techniques or ligand-binding assays.

The specific genes useful for the detecting method of the invention are TNFα, IL-1b, IL-10, CCL2, interferon beta (IFN-β), IL-17, IL-2, IL-4 and VEGF.

The term "TNF-alpha" (or abbreviated as "TNF-α", "TNFα" or simply "TNF"), as used herein, is intended to refer to a gene which in humans encodes a cytokine that exists as a 17 kD secreted form and a 26 kD membrane associated form, the biologically active form of which is composed of a trimer of non-covalently bound 17 kD molecules. The human gene is shown in the Ensembl database under accession number ENSG00000232810 (Ensemble release 99, January 2020). The term "TNF-alpha" as used herein not only includes the human gene and protein but also their orthologues from other species such as dogs, mice, rats, etc., as well as functionally equivalent variants thereof. In an embodiment, the level of TNF-alpha expression in the blood of a subject with bacteremia is lower than the reference value expression of said marker.

In a particular embodiment, the level of TNF-alpha expression in the blood of a subject with bacteremia is lower than 500 pg/ml, lower than 450 pg/ml, lower 350 pg/ml, than 300 pg/ml, lower than 250 pg/ml lower than 200 pg/ml lower than 150 pg/ml lower than 100 pg/ml, lower than 75 pg/ml lower than 50 pg/ml, lower than 25 pg/ml lower than 10 pg/ml, lower than 5 pg/ml.

In another embodiment, when the bacteremia is caused by a respiratory infection, then, the level of TNF-alpha expression in the blood of a subject with bacteremia is lower than 500 pg/ml, lower than 450 pg/ml, lower 350 pg/ml, than 300 pg/ml, lower than 250 pg/ml lower than 200 pg/ml, lower than 150 pg/ml, lower than 100 pg/ml, lower than 75 pg/ml, lower than 50 pg/ml, lower than 25 pg/ml. In a more particular embodiment, when the bacteremia is caused by a respiratory infection, the level of TNF-alpha expression in the blood of a subject with bacteremia is lower than 500 pg/ml, lower than 450 pg/ml, lower 350 pg/ml, than 300 pg/ml, lower than 250 pg/ml, lower than 200 pg/ml, lower than 150 pg/ml but higher than 100 pg/ml. In a more particular embodiment, when the bacteremia is caused by a respiratory infection, the level of TNF-alpha expression in the blood of a subject with bacteremia is lower than 500 pg/ml, lower than 450 pg/ml, lower 350 pg/ml, than 300 pg/ml, lower than 250 pg/ml, lower than 200 pg/ml but higher than 50 pg/ml.

In another particular embodiment, when the bacteremia is produced by a urinary or abdominal infection, then the level of TNF-alpha expression in the blood of a subject with bacteremia is lower than 300 pg/ml, lower than 250 pg/ml lower than 200 pg/ml, lower than 150 pg/ml, lower than 100 pg/ml, lower than 75 pg/ml, lower than 50 pg/ml, lower than 25 pg/ml lower than 10 pg/ml, lower than 5 pg/ml.

The term "respiratory infection" or "acute respiratory infection" refers to an infection, or an illness showing symptoms and/or physical findings consistent with an infection (e.g., symptoms such as coughing, wheezing, fever, sore throat, congestion; physical findings such as elevated heart rate, elevated breath rate, abnormal white blood cell count, low arterial carbon dioxide tension ($PaCO_2$), etc.), of the upper or lower respiratory tract, often due to a bacterial or viral pathogen, and characterized by rapid progression of symptoms over hours to days. Respiratory infections may primarily be of the upper respiratory tract (URIs), the lower respiratory tract (LRIs), or a combination of the two. Respiratory infections may have systemic effects due to spread of the infection beyond the respiratory tract or due to collateral damage induced by the immune response. An example of the former includes *Staphylococcus aureus* pneumonia that has spread to the blood stream and can result in secondary sites of infection, including endocarditis (infection of the heart valves), septic arthritis (joint infection), or osteomyelitis (bone infection). An example of the latter includes influenza pneumonia leading to acute respiratory distress syndrome and respiratory failure.

The term "urinary infection" or "urinary tract infection" or "UTI" refers to a bacterial infection that affects parts of the body that produce and/or carry urine, i.e. the urinary tract, e.g. kidney, ureter, bladder and/or urethra. When it affects the lower urinary tract it is also known as a bladder infection (cystitis), and when it infects the upper urinary tract it is also known as kidney infection (pyelonephritis). Symptoms from a lower UTI can include pain with urination, frequent urination, and feeling the need to urinate despite having an empty bladder, while symptoms of kidney infection can include fever and flank pain usually in combination with the symptoms of a lower UTI. UTI can also lead to life-threatening invasive *E. coli* disease, e.g. bacteremia, sepsis, or urosepsis. The most common cause of UTI is *E. coli*. The term "abdominal infection" or "intra-abdominal infections" or "IAI" refers to peritoneal inflammation in response to microorganisms, resulting in pus in the peritoneal cavity. Based on the extent of the infection, IAIs are classified as uncomplicated or complicated. Uncomplicated IAIs involve intramural inflammation of the gastrointestinal (GI) tract without anatomic disruption. Complicated IAIs involve infections that have extended beyond the source organ into the peritoneal space. Complicated IAIs cause peritoneal inflammation, and are associated with localized or diffuse peritonitis. Examples of IAIs include inflammatory bowel disease (IBD) and Crohn's disease.

The term "Interleukin-1β" (IL-1β) refers to a gene which in humans encodes a 17 kDa secreted proinflammatory cytokine that is involved in the acute phase response and is a pathogenic mediator of many diseases. IL-1β protein is normally produced by macrophages and epithelial cells. IL-1β is also released from cells undergoing apoptosis. The human gene is shown in the Ensembl database under accession number ENSG00000125538 (Ensembl release 99, January 2020). In an embodiment, the level of IL-1β expression in the blood of a subject with bacteremia is lower than the reference value expression of said marker. In a particular embodiment, the level of IL-1β expression in the blood of a subject with bacteremia is lower than 50 pg/ml, lower than 40 pg/ml, lower than 30 pg/ml, lower than 20 pg/ml, lower than 10 pg/ml, lower than 5 pg/ml or lower than 1 pg/ml.

The term "interferon-β" (IFN-β) refers to a gene encoding a cytokine that belongs to the interferon family of signaling proteins, which are released as part of the innate immune response to pathogens. The protein encoded by this gene belongs to the type I class of interferons, which are important for defense against viral infections. In addition, type I interferons are involved in cell differentiation and anti-tumor defenses. The human gene is shown in the Ensembl database under accession number ENSG00000171855 (Ensembl release 99, January 2020). In an embodiment, the level of IFN-β expression in the blood of a subject with bacteremia is lower than the reference value expression of said marker.

The term "interleukin-17" (Cytotoxic T-Lymphocyte-Associated Serine Esterase 8) or IL-17 refers to a gene encoding a proinflammatory cytokine produced by activated T cells. This cytokine regulates the activities of NF-kappaB and mitogen-activated protein kinases. This cytokine can stimulate the expression of IL-6 and cyclooxygenase-2 (PTGS2/COX-2), as well as enhance the production of nitric oxide (NO). The human gene is shown in the Ensembl database under accession number ENSG00000112115 (Ensembl release 99, January 2020). In an embodiment, the level of IL-17 expression in the blood of a subject with bacteremia is higher than the reference value expression of said marker.

The term "Interleukin-10" (IL-10) refers to a gene encoding a cytokine produced primarily by monocytes and to a lesser extent by lymphocytes. This cytokine has pleiotropic effects in immunoregulation and inflammation. It down-regulates the expression of Th1 cytokines, MHC class II Ags, and costimulatory molecules on macrophages. It also enhances B cell survival, proliferation, and antibody production. The human gene is shown in the Ensembl database under accession number ENSG00000136634 (Ensembl release 99, January 2020). In an embodiment, the level of IL-10 expression in the blood of a subject with bacteremia is higher than the reference value expression of said marker.

In a particular embodiment, the level of IL-10 expression in the blood of a subject with bacteremia is higher than 2 pg/ml, higher than 3 pg/ml, higher than 4 pg/ml, higher than 5 pg/ml, higher than 6 pg/ml, higher than 8 pg/ml, higher than 10 pg/ml, higher than 50 pg/ml, higher than 100 pg/ml, higher than 200 pg/ml, higher than 500 pg/ml.

In another embodiment, when the bacteremia is produced by a respiratory infection, then, the level of IL-10 expression in the blood of a subject with bacteremia is higher than 2 pg/ml, higher than 3 pg/ml, higher than 4 pg/ml, higher than 5 pg/ml, higher than 6 pg/ml, higher than 8 pg/ml, higher than 10 pg/ml, higher than 50 pg/ml, higher than 100 pg/ml, higher than 200 pg/ml, higher than 500 pg/ml. In a more particular embodiment, when the bacteremia is produced by a respiratory infection, then, the level of IL-10 expression in the blood of a subject with bacteremia is higher than 2 pg/ml, higher than 3 pg/ml, higher than 4 pg/ml, higher than 5 pg/ml, higher than 6 pg/ml, higher than 8 pg/ml, higher than 10 pg/ml, but lower than 20 pg/ml.

In another particular embodiment, when the bacteremia is produced by a urinary or abdominal infection, then, the level of IL-10 expression in the blood of a subject with bacteremia is higher than 2 pg/ml, higher than 3 pg/ml, higher than 4 pg/ml, higher than 5 pg/ml, higher than 6 pg/ml, higher than 8 pg/ml, higher than 10 pg/ml, higher than 50 pg/ml, higher than 100 pg/ml, higher than 200 pg/ml, higher than 500 pg/ml. In a more particular embodiment, when the bacteremia is produced by a urinary or abdominal infection, then, the level of IL-10 expression in the blood of a subject with bacteremia is higher than 20 pg/ml.

The term "CCL2", (also called Macrophage Chemotactic Protein-1 or MCP-1) refers to a gene encoding a chemokine that in many cases displays chemotactic activity for monocytes and basophils. CCL2 is particularly highly expressed during inflammation, and is a potent monocyte as well as a lymphocyte chemoattractant. CCL2 activates CCR2 on rolling monocytes, triggering integrin mediated arrest. CCL2 is also one of the strongest histamine inducing factors. The human gene is shown in the Ensembl database under accession number ENSG00000108691 (Ensembl release 99, January 2020). In an embodiment, the level of CCL2 expression in the blood of a subject with bacteremia is higher than the reference value expression of said marker.

In a particular embodiment, the level of CCL2 expression in the blood of a subject with bacteremia is higher than 6.0 ng/ml, higher than 6.5 ng/ml, higher than 7.0 ng/ml, higher than 7.5 ng/ml, higher than 8.0 ng/ml, higher than 8.5 ng/ml, higher than 9.0 ng/ml, higher than 9.5 ng/ml, higher than 10.0 ng/ml higher than 50.0 ng/ml.

The term, "Interleukin-2" or "IL-2" makes reference to a gene encoding a secreted cytokine that is important for the proliferation of T and B lymphocytes. The receptor of this cytokine is a heterotrimeric protein complex whose gamma chain is also shared by interleukin 4 (IL-4) and interleukin 7 (IL-7). The expression of this gene in mature thymocytes is monoallelic, which represents an unusual regulatory mode for controlling the precise expression of a single gene. The human gene is shown in the Ensembl database under accession number ENSG00000109471 In an embodiment, the level of IL-2 expression in the blood of a subject with bacteremia is higher than the reference value expression of said marker.

The term "interleukin-4" or "IL-4" refers to a pleiotropic cytokine produced by activated T cells. This cytokine is a ligand for interleukin 4 receptor. The interleukin 4 receptor also binds to IL-13, which may contribute to many overlapping functions of this cytokine and IL-13. STAT6, a signal transducer and activator of transcription, has been shown to play a central role in mediating the immune regulatory signal of this cytokine. The human gene is shown in the Ensembl database under accession number ENSG00000113520 (Ensembl release 99, January 2020). In an embodiment, the level of IL-4 expression in the blood of a subject with bacteremia is higher than the reference value expression of said marker.

The term "VEGF" or "Vascular Endothelial Growth Factor" refers to a member of the PDGF/VEGF growth factor family, which encodes a heparin-binding protein, which exists as a disulfide-linked homodimer. This growth factor induces proliferation and migration of vascular endothelial cells, and is essential for both physiological and pathological angiogenesis. The human gene is shown in the Ensembl database under accession number ENSG00000112715 (Ensembl release 99, January 2020). In an embodiment, the level of VEGF expression in the blood of a subject with bacteremia is higher than the reference value expression of said marker.

The diagnostic method of the invention comprises/involves comparing the expression level of the specific genes with a reference value.

The term "reference value", as used herein, relates to a predetermined criteria used as a reference for evaluating the values or data obtained from the blood samples collected from a subject. The reference value or reference level can be an absolute value, a relative value, a value that has an upper or a lower limit, a range of values, an average value, a median value, a mean value, or a value as compared to a particular control or baseline value. A reference value can be based on an individual blood sample value, such as for example, a value obtained from a sample from the subject being tested, but at an earlier point in time. The reference value can be based on a large number of blood samples, such as from a population of subjects of the chronological age matched group, or based on a pool of samples including or excluding the sample to be tested.

The reference value according to the first method of the invention can be obtained from one or more subjects who do not suffer from bacteremia (i.e., control subjects). A subject is considered to not suffer from bacteremia if they have not been diagnosed with bacteremia. The diagnosis of bacteremia can be typically done by culturing a blood sample. In a particular embodiment, the reference value for the first method of the invention is obtained from one or more subjects who suffer from SIRS but who do not suffer from an infection, and in particular, who have not been diagnosed as having bacteremia. In a particular embodiment, when the subject suffers from SIRS, the reference value for the first method of the invention can be obtained from one or more subjects who suffer from SIRS but who do not suffer from an infection, and in particular, who have not been diagnosed as having bacteremia. In a particular embodiment, when the subject suffers from CF, the reference value for the first method of the invention can be obtained from one or more subjects who suffer from SIRS but who do not suffer from an infection, and in particular, who have not been diagnosed as having bacteremia or from one or more subjects who suffer from CF but who have not been diagnosed as having bacterial pulmonary exacerbation. In another particular embodiment, when the subject suffers from CF, the reference value for the first method of the invention can be obtained from a sample from one or more subjects who suffer from bacteremia, in particular, who suffer from bacteremia caused by a respiratory infection.

In a particular embodiment the reference value is obtained from a blood sample of a subject or subjects, as described above, who do not suffer from bacteremia and that has been in contact with a TLR4 inhibitor in a similar way as the samples of the subjects suspected of suffering from bacteremia.

According to the method of the invention, the expression level of a gene is considered “decreased” when the expression level of said gene in a sample is lower than its reference value. The expression level of a gene is considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

Likewise, in the context of the method of the invention, the expression level of a gene is considered “increased” when the expression level of said gene in a sample is higher than its reference value. The expression level of a gene is considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more higher than its reference value.

The expression “is indicative”, “detection”, “diagnosing”, “diagnosis” or derivatives of the words, are used herein indistinctly and refer to the identification of the presence or characteristic of a pathological condition. It refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual’s condition into separate and distinct categories that allow medical decisions about treatment and prognosis to be made. As the person skilled in the art will understand, such a diagnosis may not be correct for 100% of the subjects to diagnose, although it is preferred if it is. The term, however, requires that a statistically significant part of the subjects can be identified as suffering from a disease, particularly bacteremia or sepsis in the context of the invention. The skilled in the art may determine whether a party is statistically significant using different statistical evaluation tools well known, for example, by determination of confidence intervals, the p-value determination, Student’s-test, the Mann-Whitney, etc. Preferred confidence intervals are at least, 50%, at least 60%, at least 70%, at least 80%, at least 90%) or at least 95%. The p-values are preferably, 0.05, 0.025, 0.001 or lower.

In an embodiment, the first method of the invention comprises determining the expression level of one of the markers selected from TNF-alpha, IL-1P, IL-10 or CCL2.

In a particular embodiment, the first method of the invention comprises determining the expression level of TNF-alpha and optionally, one or more of the markers selected from IL-1β, IL-10 or CCL2.

In another particular embodiment, the first method of the invention comprises determining the expression level of one of the markers selected from TNF-alpha, IL-1β, IL-17, IFN-β, IL-10, CCL2, IL-2, IL-4 and VEGF. In a particular embodiment, the first method of the invention comprises determining the expression level of TNF-alpha and optionally, one or more of the markers selected from IL-1β, IL-17, IFN-β, IL-10, CCL2, IL-2, IL-4 and VEGF.

In another embodiment, the first method of the invention comprises determining at least the expression level of two biomarkers selected from TNF-alpha, IL-1β, IL-10 or CCL2. In a particular embodiment, said two biomarkers are: TNF-alpha and IL-1β, TNF-alpha and IL-10, TNF-alpha and CCL2, IL-1β and IL-10, IL-1β and CCL2 or IL-10 and CCL2.

In another particular embodiment said two biomarkers are selected from TNF-alpha, IL-1β, IL-17, IFN-β, IL-10, CCL2, IL-2, IL-4 and VEGF. In a particular embodiment, said biomarkers are: TNF-alpha and IL-17; TNF-alpha and IFN-β; TNF-alpha and IL-2; TNF-alpha and IL-4; TNF-alpha and VEGF; IL-1β and IL-17; IL-1β and INF-β; IL-1β and IL-2; IL-1β and IL-4; IL-1β and VEGF; IL-10 and IL-17; IL-10 and INF-β; IL-10 and IL-2; IL10 and IL-4; IL10 and VEGF; CCL2 and IL-17; CCL2 and INF-β; CCL2 and IL-2; CCL2 and IL-4; CCL2 and VEGF; IL-17 and IFN-β; IL-17 and IL-10; IL-17 and IL-2; IL-17 and IL-4; IL-17 and VEGF; IFN-β and IL-2; IFN-β and IL-4; IFN-β and VEGF; IL-2 and IL-4; IL-2 and VEGF; or, IL-4 and VEGF.

In another particular embodiment, the first method of the invention comprises determining the expression level of at least three biomarkers selected from TNF-alpha, IL-1β, IL-10 or CCL2. In a particular embodiment, said three biomarkers are TNF-alpha, IL-1β, and IL-10; TNF-alpha, IL-1beta and CCL2; and, IL-1β, IL-10 and CCL2.

In another particular embodiment, the at least three biomarkers are selected from TNF-alpha, IL-1β, IL-17, IFN-β, IL-10, CCL2, IL-2, IL-4 and VEGF. In a particular embodiment said three biomarkers are: TNF-alpha, IL-1β and IL-17; TNF-alpha, IL-1β and IFN-β; TNF-alpha, IL-1β and IL-2; TNF-alpha, IL-1β and IL-4; TNF-alpha, IL-1β and VEGF; TNF-alpha, IL-10 and IL-17; TNF-alpha, IL-10 and IL-2; TNF-alpha, IL-10 and IL-4; TNF-alpha, IL-10 and VEGF; TNF-alpha, CCL2 and IL-17; TNF-alpha, CCL2 and IFN-β; TNF-alpha, CCL2 and IL-2; TNF-alpha, CCL2 and IL-4; and, TNF-alpha, CCL2 and VEGF.

In another particular embodiment, the first method of the invention comprises determining the expression level of the four biomarkers TNF-alpha, IL-1β, IL-10 or CCL2. In another particular embodiment, said four biomarkers are selected from TNF-alpha, IL-1β, IL-17, IFN-β, IL-10, CCL2, IL-2, IL-4 and VEGF.

In another particular embodiment, the first method of the invention comprises determining the expression level of at least five biomarkers selected from TNF-alpha, IL-1β, IL-17, IFN-β, IL-10, CCL2, IL-2, IL-4 and VEGF.

In another particular embodiment, the first method of the invention comprises determining the expression level of at least, six, at least, seven, at least eight or at least nine biomarkers selected from TNF-alpha, IL-1β, IL-17, IFN-β, IL-10, CCL2, IL-2, IL-4 and VEGF.

In a particular embodiment, if bacteremia is detected with the method of the invention, and the subject suffers from systemic inflammatory response syndrome (SIRS), the subject is diagnosed to suffer from sepsis.

The term "Systemic inflammatory response syndrome" (SIRS) refers to an inflammatory state affecting the whole body. It is the body's response to an infectious or noninfectious insult. Four SIRS criteria have been defined, namely tachycardia (heart rate>90 beats/min), tachypnea (respiratory rate>20 breaths/min), fever or hypothermia (temperature>38 or <36° C.), and leukocytosis, leukopenia, or bandemia (white blood cells>1,200/mm3, <4,000/mm3 or band cell count≥10%). Patients who met two or more of these criteria fulfilled the definition of SIRS. A skilled in the art will be able to diagnose a subject with SIRS and to take into consideration any deviation from the standard criteria for the diagnosis of SIRS. When SIRS is caused by infection, the infection is termed sepsis which, has progressively severe stages (severe sepsis, and septic shock).

Therefore, in a particular embodiment, if the subject suffers from SIRS and bacteremia is detected, the subject is diagnosed to suffer from sepsis.

The term "sepsis" refers to a life-threatening organ dysfunction caused by a dysregulated host response to infection, which is usually confirmed by the presence of SIRS further accompanied by a clinically evident of microbiologically confirmed infection. This infection may be bacterial, fungal, parasitic or viral. Within the context of the present invention, the term "sepsis" relates to all the different stages of the disease, that is sepsis, severe sepsis and septic shock, as known by a skilled in the art.

The term "Severe sepsis" refers to a subset of sepsis patients, in which sepsis is further accompanied by organ hypoperfusion made evident by at least one sign of organ dysfunction such as hypoxemia, oliguria, metabolic acidosis, or altered cerebral function.

The term, "Septic shock" refers to a subset of severe sepsis patients, in which severe sepsis is further accompanied by hypotension, made evident by a systolic blood pressure<90 mm Hg, or the requirement for pharmaceutical intervention to maintain blood pressure.

In a particular embodiment, the sepsis is caused by bacteria. In another embodiment, the bacteria are gram-positive bacteria. In another embodiment, the bacteria are gram-negative bacteria.

Within the context of the present invention, any of the non-limiting examples of bacteria mentioned with regard to bacteremia can be the cause of the sepsis. In general, as mentioned above, an untreated bacteremia can potentially lead to the development of SIRS and therefore, to sepsis.

In another embodiment, if bacteremia is detected and the subject suffers from cystic fibrosis, then, the subject is diagnosed to have bacterial pulmonary exacerbation.

The term "cystic fibrosis" (CF) refers to an autosomal recessive genetic disorder that affects mostly the lungs, but also the pancreas, liver, kidneys, and intestine. Long-term issues include difficulty breathing and coughing up mucus as a result of frequent lung infections. CF is caused by a mutation in the gene cystic fibrosis transmembrane conductance regulator (CFTR). The most common mutation, ΔF508, is a deletion (Δ signifying deletion) of three nucleotides that results in a loss of the amino acid phenylalanine (F) at the 508th position on the protein. However, over 1500 other mutations can produce CF. Although most people have two working copies (alleles) of the CFTR gene, only one is needed to prevent cystic fibrosis.

The term "bacterial pulmonary exacerbation", as used herein, refers to an episode of acute worsening of symptoms in a patient with cystic fibrosis due to the presence of a bacterial infection. Pulmonary exacerbation signs and symptoms include increased cough, increased sputum production, fever, weight loss, increased respiratory rate, new findings on chest auscultation, decreased exercise tolerance or fatigue, decrease in $FEV_1$ (forced expiratory volume in one second) of 10% predicted, decrease in pulse oximetry and infiltrates on chest radiography. A skilled in the art or medical practitioner will have the knowledge to detect and diagnose bacterial pulmonary exacerbations. Additional definitions and characteristics of bacterial pulmonary exacerbations can be found in Jayesh M. Bhatt, European Respiratory Review 2013, vol 22, 205-2016 and in Waters V and Ratjen F, Ann Am Thorac Soc. 2015 November; 12 Suppl 2:S200-6. In a particular embodiment, bacterial pulmonary exacerbation can be diagnosed with the following diagnostic criteria:

(i) When a patient with CF has any 4 of the following 12 signs or symptoms defined by Fuchs et al., N Engl J Med. 1994 Sep. 8; 331(10):637-42.
- change in sputum;
- new or increased hemoptysis;
- increased cough;
- increased dyspnea;
- malaise, fatigue or lethargy;
- temperature over 38° C.;
- anorexia or weight loss;
- sinus pain or tenderness;
- change in sinus discharge;
- change in physical examination of the chest;
- decrease in pulmonary function by 10 percent or more from a previously recorded value;
- radiographic changes indicative or pulmonary infection.

(ii) One of the major criteria alone or two of the minor signs/symptoms and fulfillment of symptom duration, as defined by Treggiari et al, Contemp Clin Trials 2009; 30: 256-268.

Major Criteria
1. Decrease in $FEV_1$ of ≥10% from best baseline within past 6 months, unresponsive to albuterol (in participants able to reproducibly perform spirometry).
2. Oxygen saturation<90% on room air or ≥5% decline from previous baseline.
3. New lobar infiltrate(s) or atelectasi(e)s on chest radiograph.
4. Hemoptysis (more than streaks on more than one occasion in past week.

Minor sings/symptoms
1. Increased work of breathing or respiratory rate
2. New or increased adventitial sounds on lung exam.
3. Weight loss≥5% of body weight or decrease across 1 major percentile in weight percentile for age in past 6 months.
4. Increased cough.
5. Decreased exercise tolerance or level of activity.
6. Increased chest congestion or change in sputum.

Sings/symptoms fulfillment

1. Duration of sing/symptoms≥5 days or significant symptom severity.

In an embodiment, when the subject suffers from CF, the level of TNF-alpha expression in the blood of a subject with bacteremia or bacterial pulmonary exacerbation is lower than 500 pg/ml, lower than 450 pg/ml, lower 350 pg/ml, than 300 pg/ml, lower than 250 pg/ml lower than 200 pg/ml, lower than 150 pg/ml, lower than 100 pg/ml, lower than 75 pg/ml, lower than 50 pg/ml, lower than 25 pg/ml. In a more particular embodiment, when the subject suffers from CF, the level of TNF-alpha expression in the blood of a subject with bacteremia or bacterial pulmonary exacerbation is lower than 500 pg/ml, lower than 450 pg/ml, lower 350 pg/ml, than 300 pg/ml, lower than 250 pg/ml, lower than 200 pg/ml, lower than 150 pg/ml but higher than 100 pg/ml. In a more particular embodiment, when the subject suffers from CF, the level of TNF-alpha expression in the blood of a subject with bacteremia or bacterial pulmonary exacerbation is lower than 500 pg/ml, lower than 450 pg/ml, lower 350 pg/ml, than 300 pg/ml, lower than 250 pg/ml, lower than 200 pg/ml but higher than 150 pg/ml.

In another embodiment, when the subject suffers from CF, the level of IL-1β expression in the blood of a subject with bacteremia or bacterial pulmonary exacerbation is lower than 50 pg/ml, lower than 40 pg/ml, lower than 30 pg/ml, lower than 20 pg/ml, lower than 10 pg/ml, lower than 0.5 pg/ml or lower than 0.1 pg/ml.

In another embodiment, when the subject suffers from CF, then, the level of IL-10 expression in the blood of a subject with bacteremia or bacterial pulmonary exacerbation is higher than 2 pg/ml, higher than 3 pg/ml, higher than 4 pg/ml, higher than 5 pg/ml, higher than 6 pg/ml, higher than 8 pg/ml, higher than 10 pg/ml, higher than 50 pg/ml, higher than 100 pg/ml, higher than 200 pg/ml, higher than 500 pg/ml. In a more particular embodiment, when subject suffers from CF, then, the level of IL-10 expression in the blood of a subject with bacteremia or bacterial pulmonary exacerbation is higher than 2 pg/ml, higher than 3 pg/ml, higher than 4 pg/ml, higher than 5 pg/ml, higher than 6 pg/ml, higher than 8 pg/ml, higher than 10 pg/ml, but lower than 20 pg/ml.

In another embodiment, when the subject suffers from CF, then, the level of CCL2 expression in the blood of a subject with bacteremia or bacterial pulmonary exacerbation is higher than 6.0 ng/ml, higher than 6.5 ng/ml, higher than 7.0 ng/ml, higher than 7.5 ng/ml, higher than 8.0 ng/ml, higher than 8.5 ng/ml, higher than 9.0 ng/ml, higher than 9.5 ng/ml, higher than 10.0 ng/ml higher than 50.0 ng/ml.

In a particular embodiment, the first method of the invention further comprises the determination of the expression level of at least one additional gene selected from the group consisting of the genes of Table 1.

TABLE 1

Additional biomarkers to be used in the methods of the invention

| Gene | Abbreviation |
|---|---|
| Brain-Derived Neurotrophic Factor | BDNF |
| Eotaxin-1 | Eotaxin-1 |
| Factor VII | Factor VII |
| Granulocyte-Macrophage Colony-Stimulating Factor | GM-CSF |
| Intercellular Adhesion Molecule 1 (soluble) | sICAM-1 |
| Interferon gamma | IFNG |
| Interleukin-1 alpha | IL-1A |
| Interleukin-1 receptor antagonist | IL-1RA |
| Interleukin-3 | IL-3 |
| Interleukin-5 | IL-5 |
| Interleukin-7 | IL-7 |
| Interleukin-15 | IL-15 |
| Interleukin-18 | IL-18 |
| Interleukin-23 | IL-23 |
| Macrophage Inflammatory Protein-1 alpha | MIP-1A |
| Macrophage Inflammatory Protein-1 beta | MIP-1B |
| Matrix Metalloproteinase-3 | MMP3 |
| Matrix Metalloproteinase-9 | MMP9 |
| Stem Cell Factor | SCF |
| Tumor Necrosis Factor beta | TNF-B |

The term "Brain-Derived Neurotrophic Factor" or "BDNF" refers to gene encoding a member of the nerve growth factor family of proteins. Alternative splicing results in multiple transcript variants, at least one of which encodes a preproprotein that is proteolytically processed to generate the mature protein. Binding of this protein to its cognate receptor promotes neuronal survival in the adult brain. The human gene is shown in the Ensembl database under accession number ENSG00000176697 (Ensembl release 99, January 2020). In an embodiment, the expression level of BDNF in the blood of a subject with bacteremia is higher than the reference expression value of said gene. In another embodiment, the expression level of BDNF in the blood of a subject with bacteremia is lower than the reference expression value of said gene.

The term "Eotaxin-1" or "C—C Motif Chemokine Ligand 11" refers to a gene encoding a chemokine, member of the CC subfamily, which displays chemotactic activity for eosinophils, but not mononuclear cells or neutrophils. The human gene is shown in the Ensembl database under accession number ENSG00000172156 (Ensembl release 99, January 2020). In an embodiment, the expression level of Eotaxin-1 in the blood of a subject with bacteremia is higher than the reference expression value of said gene. In another embodiment, the expression level of Eotaxin-1 in the blood of a subject with bacteremia is lower than the reference expression value of said gene.

The term "Factor VII" or "FVII Coagulation Protein" refers to a gene encoding a coagulation factor VII which is a vitamin K-dependent factor essential for hemostasis. Defects in this gene can cause coagulopathy. The human gene is shown in the Ensembl database under accession number ENSG00000057593 (Ensembl release 99, January 2020). In an embodiment, the expression level of Factor VII in the blood of a subject with bacteremia is higher than the reference expression value of said gene. In another embodiment, the expression level of Factor VII in the blood of a subject with bacteremia is lower than the reference expression value of said gene.

The term "Granulocyte-Macrophage Colony-Stimulating Factor" or "GM-CSF" refers to a gene encoding a cytokine that controls the production, differentiation, and function of granulocytes and macrophages. The active form of the protein is found extracellularly as a homodimer. The human gene is shown in the Ensembl database under accession number ENSG00000164400 (Ensembl release 99, January 2020). In an embodiment, the expression level of GM-CSF in the blood of a subject with bacteremia is higher than the reference expression value of said gene. In another embodiment, the expression level of GM-CSF in the blood of a subject with bacteremia is lower than the reference expression value of said gene.

The term "Soluble intercellular adhesion molecule-1" or "sICAM-1" represents a gene encoding a circulating form of ICAM-1 that is constitutively expressed or is inducible on the cell surface of different cell lines. It serves as a counter-receptor for the lymphocyte function-associated antigen (LFA-1). Interaction between ICAM-1, present on endothelial cells, and LFA-1 facilitates leukocyte adhesion and migration across the endothelium. The human gene is shown in the Ensembl database under accession number ENSG00000090339 (Ensembl release 99, January 2020). In an embodiment, the expression level of sICAM-1 in the blood of a subject with bacteremia is higher than the reference expression value of said gene. In another embodiment, the expression level of sICAM-1 in the blood of a subject with bacteremia is lower than the reference expression value of said gene.

The term "Interferon gamma" or "IFNG" refers to a gene encoding a soluble cytokine that is a member of the type II interferon class, secreted by cells of both the innate and adaptive immune systems. The active protein is a homodimer that binds to the interferon gamma receptor that triggers a cellular response to viral and microbial infections. The human gene is shown in the Ensembl database under accession number ENSG00000111537 (Ensembl release 99, January 2020). In an embodiment, the expression level of IFNG in the blood of a subject with bacteremia is higher than the reference expression value of said gene. In another embodiment, the expression level of IFNG in the blood of a subject with bacteremia is lower than the reference expression value of said gene.

The term "interleukin-1 alpha" or IL-1A cytokine make reference to a gene encoding a pleiotropic cytokine involved in various immune responses, inflammatory processes, and hematopoiesis. This cytokine is produced by monocytes and macrophages as a proprotein, which is proteolytically processed and released in response to cell injury, and thus induces apoptosis. The human gene is shown in the Ensembl database under accession number ENSG00000115008 (Ensembl release 99, January 2020). In an embodiment, the expression level of IL-1A in the blood of a subject with bacteremia is higher than the reference expression value of said gene. In another embodiment, the expression level of IL-1A in the blood of a subject with bacteremia is lower than the reference expression value of said gene.

The term "Interleukin-1 receptor antagonist" or "IL-1 RA" refers to a gene encoding a member of the interleukin 1 cytokine family. This protein inhibits the activities of interleukin 1, alpha (IL-1A) and interleukin 1, beta (IL-1B), and modulates a variety of interleukin 1 related immune and inflammatory responses. The human gene is shown in the Ensembl database under accession number ENSG00000136689 (Ensembl release 99, January 2020). In an embodiment, the expression level of IL-1 RA in the blood of a subject with bacteremia is higher than the reference expression value of said gene. In another embodiment, the expression level of IL-1RA in the blood of a subject with bacteremia is lower than the reference expression value of said gene.

The term "Interleukin 3" or "IL-3" refers to a gene encoding a growth promoting cytokine. This cytokine is capable of supporting the proliferation of a broad range of hematopoietic cell types. It is involved in a variety of cell activities such as cell growth, differentiation and apoptosis. The human gene is shown in the Ensembl database under accession number ENSG00000164399 (Ensembl release 99, January 2020). In an embodiment, the expression level of IL-3 in the blood of a subject with bacteremia is higher than the reference expression value of said gene. In another embodiment, the expression level of IL-3 in the blood of a subject with bacteremia is lower than the reference expression value of said gene.

The term "Interleukin 5" or "IL-5" refers to a gene encoding a cytokine that acts as a growth and differentiation factor for both B cells and eosinophils. The encoded cytokine plays a major role in the regulation of eosinophil formation, maturation, recruitment and survival. The increased production of this cytokine may be related to pathogenesis of eosinophil-dependent inflammatory diseases. The human gene is shown in the Ensembl database under accession number ENSG00000113525 (Ensembl release 99, January 2020). In an embodiment, the expression level of IL-5 in the blood of a subject with bacteremia is higher than the reference expression value of said gene. In another embodiment, the expression level of IL-5 in the blood of a subject with bacteremia is lower than the reference expression value of said gene.

The term "Interleukin-7" or "IL-7" refers to a gene encoding a cytokine important for B and T cell development. This cytokine and the hepatocyte growth factor (HGF) form a heterodimer that functions as a pre-pro-B cell growth-stimulating factor. This cytokine is found to be a cofactor for V(D)J rearrangement of the T cell receptor beta (TCRB) during early T cell development. The human gene is shown in the Ensembl database under accession number ENSG00000104432 (Ensembl release 99, January 2020). In an embodiment, the expression level of IL-7 in the blood of a subject with bacteremia is higher than the reference expression value of said gene. In another embodiment, the expression level of IL-7 in the blood of a subject with bacteremia is lower than the reference expression value of said gene.

The term "Interleukin-15" or "IL-15" refers to a gene encoding a cytokine that regulates T and natural killer cell activation and proliferation. This cytokine and interleukin 2 share many biological activities. They are found to bind common hematopoietin receptor subunits, and may compete for the same receptor, and thus negatively regulate each other's activity. The human is shown in the Ensembl database under accession number ENSG00000164136 (Ensembl release 99, January 2020). In an embodiment, the expression level of IL-15 in the blood of a subject with bacteremia is higher than the reference expression value of said gene. In another embodiment, the expression level of IL-15 in the blood of a subject with bacteremia is lower than the reference expression value of said gene.

The term "Interleukin-18" or "IL-18" refers to a gene encoding a proinflammatory cytokine primarily involved in polarized T-helper 1 (Th1) cell and natural killer (NK) cell immune responses. Upon binding to IL18R1 and IL18RAP, forms a signaling ternary complex that activates NF-kappa-B, triggering synthesis of inflammatory mediators. The human gene is shown in the Ensembl database under accession number ENSG00000164136 (Ensembl release 99, January 2020). In an embodiment, the expression level of IL-18 in the blood of a subject with bacteremia is higher than the reference expression value of said gene. In another embodiment, the expression level of IL-18 in the blood of a subject with bacteremia is lower than the reference expression value of said gene.

The term "Interleukin-23" or "IL-23" refers to a gene encoding a heterodimeric cytokine composed of an IL12B (IL-12p40) subunit (that is shared with IL12) and the IL-23A (IL-23p19) subunit. The human genes that codify IL-12B and IL-23A subunits are shown in the Ensembl database under accession numbers ENSG00000113302 (Ensembl release 99, January 2020) and ENSG00000110944 (Ensembl release 99, January 2020) respectively. In an embodiment, the expression level of IL-23 in the blood of a subject with bacteremia is higher than the reference expression value of said gene. In another embodiment, the expression level of IL-23 in the blood of a subject with bacteremia is lower than the reference expression value of said gene.

The term "Macrophage Inflammatory Protein-1 alpha" or "MIP-1A" refers to a gene encoding a small inducible cytokine, which plays a role in inflammatory responses through binding to the receptors CCR1, CCR4 and CCR5. Polymorphisms at this locus may be associated with both resistance and susceptibility to infection by human immunodeficiency virus type 1. The human gene is shown in the Ensembl database under accession number ENSG00000277632 (Ensembl release 99, January 2020). In an embodiment, the expression level of MIP-1A in the blood of a subject with bacteremia is higher than the reference expression value of said gene. In another embodiment, the expression level of MIP-1A in the blood of a subject with bacteremia is lower than the reference expression value of said gene.

The term "Macrophage Inflammatory Protein-1 beta" or "MIP-1B" refers a gene encoding a mitogen-inducible monokine, one of the major HIV-suppressive factors produced by CD8+ T-cells. The encoded protein is secreted and has chemokinetic and inflammatory functions. The human gene is shown in the Ensembl database under accession number ENSG00000275302 (Ensembl release 99, January 2020). In an embodiment, the expression level of MIP-1B in the blood of a subject with bacteremia is higher than the reference expression value of said gene. In another embodiment, the expression level of MIP-1B in the blood of a subject with bacteremia is lower than the reference expression value of said gene.

The term "Matrix Metalloproteinase-3" or "MMP3" refers to a gene encoding an enzyme which degrades fibronectin, laminin, collagens Ill, IV, IX, and X, and cartilage proteoglycans. The enzyme is thought to be involved in wound repair, progression of atherosclerosis, and tumor initiation. The human gene is shown in the Ensembl database under accession number ENSG00000149968 (Ensembl release 99, January 2020). In an embodiment, the expression level of MMP3 in the blood of a subject with bacteremia is higher than the reference expression value of said gene. In another embodiment, the expression level of MMP3 in the blood of a subject with bacteremia is lower than the reference expression value of said gene.

The term "Matrix Metalloproteinase-9" or "MMP9" refers to a gene encoding an enzyme which degrades type IV and V collagens. It may be involved in IL-8-induced mobilization of hematopoietic progenitor cells from bone marrow, and in tumor-associated tissue remodeling. The human gene is shown in the Ensembl database under accession number ENSG00000100985 (Ensembl release 99, January 2020). In an embodiment, the expression level of MMP9 in the blood of a subject with bacteremia is higher than the reference expression value of said gene. In another embodiment, the expression level of MMP9 in the blood of a subject with bacteremia is lower than the reference expression value of said gene.

The term "Tem Cell Factor" or "SCF" or "KIT-ligand" or "KL" refers to a gene encoding a cytokine that binds to the c-KIT receptor (CD117). SCF can exist as both a transmembrane protein and a soluble protein. This cytokine plays an important role in hematopoiesis (formation of blood cells), spermatogenesis, and melanogenesis. The human gene is shown in the Ensembl database under accession number ENSG00000049130 (Ensembl release 99, January 2020). In an embodiment, the expression level of SCF in the blood of a subject with bacteremia is higher than the reference expression value of said gene. In another embodiment, the expression level of SCF in the blood of a subject with bacteremia is lower than the reference expression value of said gene.

The term "Tumor Necrosis Factor beta" or "TNF-β" or "Lymphotoxin-alpha (LT-α)" refers to a gene encoding a cytokine produced by lymphocytes. The protein is highly inducible, secreted, and forms heterotrimers with lymphotoxin-beta which anchor lymphotoxin-alpha to the cell surface. This protein also mediates a large variety of inflammatory, immunostimulatory, and antiviral responses, is involved in the formation of secondary lymphoid organs during development and plays a role in apoptosis. The human gene is shown in the Ensembl database under accession number ENSG00000226979 (Ensembl release 99, January 2020). In an embodiment, the expression level of TNF-B in the blood of a subject with bacteremia is higher than the reference expression value of said gene. In another embodiment, the expression level of TNF-B in the blood of a subject with bacteremia is lower than the reference expression value of said gene.

Methods for Selecting a Therapy

In second aspect, the invention relates to an in vitro method, hereinafter the second method of the invention, for selecting a therapy for a subject suffering from systemic inflammatory response syndrome (SIRS), comprising:

(a) contacting a blood sample from the subject with a TLR4 agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and
(c) comparing said expression level with a reference value, wherein if a decreased level of TNFα, IL-1b and/or IFN-β compared to the reference value and/or an increased level of IL-10, CCL2, IL-2, IL-4 and/or VEGF compared to the reference value is detected, a therapy with one or more broad spectrum antibiotics is selected.

The term "therapy" as used herein, refers to any remedy directed to alleviate the symptoms, diminish the extent of the disease, stabilize (i.e., not worsen) the state of disease, delay or slow disease progression, ameliorate or palliate the disease state, or achieve remission (whether partial or total) of the disease.

The term "broad-spectrum antibiotics" refers to antibiotics that acts on the two major bacterial groups, gram-positive and gram-negative, or any antibiotic that acts against a wide range of disease-causing bacteria. These medications are used when a bacterial infection is suspected but the group of bacteria is unknown (also called empiric therapy) or when infection with multiple groups of bacteria is suspected. Non-limiting examples of broad-spectrum antibiotics include quinolones (e.g. ciprofloxacin), fluoroquinolones (e.g. levofloxacin), aminoglycosides (except for streptomycin), carbapenem, piperacillin-tazobactam, aztreonam, teicoplaninsulphonamides and more particularly, ceftriaxone, azithromycin and vancomycin.

An empiric broad-spectrum therapy with one or more antimicrobials may be used to cover all likely pathogens. Coverage should be directed against both gram-positive and gram-negative bacteria and, if indicated, against fungi (eg, *Candida*) and rarely viruses (e.g., influenza). Many patients with septic shock, particularly those suspected to have gram negative sepsis, may receive combination therapy with at least two antimicrobials from two different classes (ie, combination therapy) depending on the organisms that are considered likely pathogens and local antibiotic susceptibilities. Combination therapy is defined as multiple antibiotics given with the intent of covering a known or suspected pathogen with more than one agent.

Therefore, in an embodiment, the therapy consists of a combination therapy.

Empiric therapy is usually directed to the most common organisms causing sepsis in specific patient populations. Among organisms isolated from patients with sepsis, the most common include *Escherichia coli, Staphylococcus aureus, Klebsiella pneumoniae*, and *Streptococcus pneumoniae*, such that coverage of these organisms should be kept in mind when choosing an agent.

Since the present method allows an early diagnosis of sepsis, in most diagnosed cases the microorganism causing the infection is unknown, and therefore, other potential pathogens when risk factors are present may be considered. Non-limiting examples of potential pathogens causing sepsis and possible therapies are disclosed herein.

Subjects with risk for MRSA (Methicillin-resistant *S. aureus*) may be treated with intravenous vancomycin (adjusted for renal function). Potential alternative agents to vancomycin (e.g., daptomycin for non-pulmonary MRSA, linezolid) should be considered for patients with refractory or virulent MRSA, or with a contraindication to vancomycin.

If *Pseudomonas* is a likely pathogen, combination of vancomycin with one of the following antibiotics may be used: a 3rd generation (e.g., ceftriaxone or cefotaxime) or 4th generation cephalosporin (cefepime), or a beta-lactam/beta-lactamase inhibitor (e.g., piperacillin-tazobactam, ticarcillin-clavulanate), or a carbapenem (e.g., imipenem or meropenem).

Alternatively, where *Pseudomonas* is a likely pathogen, combination of vancomycin with two of the following, depending on local antibiotic susceptibility patterns may be used: antipseudomonal cephalosporin (e.g., ceftazidime, cefepime), or antipseudomonal carbapenem (e.g., imipenem, meropenem), or antipseudomonal beta-lactam/beta-lactamase inhibitor (e.g., piperacillin-tazobactam, ticarcillin-clavulanate), or fluoroquinolone with good anti-pseudomonal activity (e.g., ciprofloxacin), or aminoglycoside (e.g., gentamicin, amikacin), or monobactam (e.g., aztreonam).

Patients with suspected non pseudomonal gram-negative organisms (e.g., *E. coli, K. pneumoniae*) may be treated with monotherapy with a single agent with proven efficacy and the least possible toxicity, such as a third generation cephalosporin or a carbapenem, except in patients who are either neutropenic or whose sepsis is due to a known or suspected *Pseudomonas* infection, where combination therapy can be considered.)

Patients with suspected invasive fungal infections may be treated with antifungals such as fluconazole, ketoconazole, anidulafungin, caspofungin, micafungin, echinocandin (for *Candida*) or voriconazole (for *Aspergillus*).

Other therapies may consider the inclusion of agents for specific organisms such as *Legionella* (macrolide or fluoroquinolone) or difficult to treat organisms (e.g., *Stenotrophomonas*), or for specific conditions (e.g., neutropenic bacteremia).

An expert in the field will know the suitable therapy in each case as well as the appropriate dose of the antimicrobial agent.

Regarding the dosing, a full "high-end" loading dose may be considered. This strategy is based upon the known increased volume of distribution that can occur in patients with sepsis due to the administration of fluid and that higher clinical success rates have been reported in patients with higher peak concentrations of antimicrobials. Continuous infusions of antibiotics as compared with intermittent dosing regimens can also be considered. Thus in an embodiment, the therapy comprises the continuous infusion of antibiotics. In another embodiment, the therapy comprises an intermittent administration of antibiotics.

In a particular embodiment, when the bacteremia is caused by a respiratory infection, the treatment comprises the intravenous administration of ceftriaxone and levofloxacin. In a more particular embodiment, the dose of ceftriaxone is of at least 0.5 g/24 h, at least 0.6 g/24 h, at least 0.7 g/24 h, at least 0.8 g/24 h, at least 0.9 g/24 h or at least 1 g/24, preferably 1 g/24 h. In another more particular embodiment, the dose of levofloxacin is of at least 250 mg/24 h, at least 300 mg/24 h, at least 350 mg/24 h, at least 400 mg/24 h, at least 450 mg/24 h or at least 500 mg/24 h, preferably 500 mg/24. In another more particular embodiment, the dose of ceftriaxone is of at least 0.5 g/24 h, at least 0.6 g/24 h, at least 0.7 g/24 h, at least 0.8 g/24 h, at least 0.9 g/24 h or at least 1 g/24, preferably 1 g/24 h and the dose of levofloxacin is of at least 250 mg/24 h, at least 300 mg/24 h, at least 350 mg/24 h, at least 400 mg/24 h, at least 450 mg/24 h or at least 500 mg/24 h, preferably 500 mg/24 h. In a particular embodiment, ceftriaxone is administered intravenously, or levofloxacin is administered intravenously. Preferably, both ceftriaxone and levofloxacin are administered intravenously.

In another particular embodiment, when the bacteremia is caused by a respiratory infection and the subject is allergic to penicillin the treatment comprises the intravenous administration of levofloxacin. In a particular embodiment, the dose of levofloxacin is of at least 250 mg/24 h, at least 300 mg/24 h, at least 350 mg/24 h, at least 400 mg/24 h, at least 450 mg/24 h or at least 500 mg/24 h, preferably 500 mg/24 h. In a more particular embodiment, the levofloxacin is administered intravenously.

In another particular embodiment, when the bacteremia does not have an identified focus of infection, or when the bacteremia is caused by a urinary of abdominal infection, the treatment comprises the intravenous administration of piperacillin/tazobactam. In a more particular embodiment, the dose of piperacillin/tazobactam is of at least 2 g/8 h, at least 3 g/8 h, at least 4 g/8 h, at least 4 g/8 h, at least 8 g/8 h, preferably 4 g/8 h. In a particular embodiment, the administration of piperacillin/tazobactam is intravenous.

In another particular embodiment, when the bacteremia does not have an identified focus of infection, or when the bacteremia is caused by a urinary of abdominal infection, and the patient is allergic to penicillin, the treatment comprises the intravenous administration aztreonam and teicoplanin. In a more particular embodiment, the dose of aztreonam is of at least 0.5 g/8 h, at least 0.6 g/8 h, at least 0.7 g/8 h, at least 0.8 g/8 h, at least 0.9 g/8 h, at least 1 g/8 h, at least 1.2 g/8 h or at least 1.5 g/8 h, preferably 1 g/8 h. In another more particular embodiment, the dose of teicoplanin is of at least 200 mg/12 h, at least 250 mg/12 h, at least 300 mg/12 h, at least 350 mg/12 h, at least 400 mg 12 h, at least 450 mg/12 h or at least 500 mg/12 h, preferably 400 mg/12 h, and preferably followed by the same dose every 24 h. In an even more particular embodiment, the dose of aztreonam is of at least 0.5 g/8 h, at least 0.6 g/8 h, at least 0.7 g/8 h, at least 0.8 g/8 h, at least 0.9 g/8 h, at least 1 g/8 h, at least 1.2 g/8 h or at least 1.5 g/8 h, preferably 1 g/8 h and the dose of teicoplanin is of at least 200 mg/12 h, at least 250 mg/12 h, at least 300 mg/12 h, at least 350 mg/12 h, at least 400 mg 12 h, at least 450 mg/12 h or at least 500 mg/12 h, preferably 400 mg/12 h, and preferably followed by the same dose every 24 h.

In a particular embodiment, aztreonam is administered intravenously. In a particular embodiment, teicoplanin is administered intravenously. Preferably, both aztreonam and teicoplanin are administered intravenously.

In another aspect, the invention relates to an in vitro method, hereinafter the third method of the invention, for selecting a therapy for a subject suffering from cystic fibrosis, comprising:

(a) contacting a blood sample from the subject with a TLR4 agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF and in the blood sample previously contacted with the TLR4 agonist and
(c) comparing said expression level with a reference value, wherein if
a decreased level of TNFα, IL-1b and/or IFN-β compared to the reference value and/or
an increased level of IL-10, CCL2, IL-2, IL-4 and/or VEGF compared to the reference value
is detected, then
if the subject is not under treatment with an antibiotic, then a therapy with one or more broad spectrum antibiotics is selected, and
if the subject is under treatment with an antibiotic, said antibiotic is replaced by a different type of antibiotic or the dosage of said antibiotic is changed.

In a particular embodiment, the subject is not under treatment with an antibiotic. The expression "the subject is not under treatment with an antibiotic" means that the subject has not been administered an antibiotic in the hour, 2 hours, 4 hours, 6 hours, 8 hours, 10 hours, 12 hours, 16 hours, 20 hours, 24 hours, 2 days, 3 days, 4 days, 5 days, 6 days, 7 days, 8 days, 9 days, 10 days, 15 days before the time at which the blood sample from the patient is obtained.

In another particular embodiment, the subject is under treatment with an antibiotic. The expression "the subject is under treatment with an antibiotic" means that the subject has been administered an antibiotic in the hour, 2 hours, 4 hours, 6 hours, 8 hours, 10 hours, 12 hours, 16 hours, 20 hours, 24 hours, 2 days, 3 days, 4 days, 5 days, 6 days, 7 days, 8 days, 9 days, 10 days, 15 days before the time at which the blood sample from the patient is obtained.

The expression "the dosage of said antibiotic is changed" means that the dosage is increased or decreased compared to the dosage of the antibiotic that the subject received in the hour, 2 hours, 4 hours, 6 hours, 8 hours, 10 hours, 12 hours, 16 hours, 20 hours, 24 hours, 2 days, 3 days, 4 days, 5 days, 6 days, 7 days, 8 days, 9 days, 10 days, 15 days before the time at which the blood sample from the patient is obtained.

The terms "in vitro", "subject", "SIRS", "cystic fibrosis", "blood sample", "TLR-4 agonist", "anticoagulant", "expression levels", "TNFα", "IL-1b", "IL-10", "CCL2", "IFN-β", "IL-17", "IL-2", "IL-4", "VEGF" and "reference value" have been previously defined in connection with the first method of the invention. All the particular and preferred embodiments regarding these terms fully apply to the second and third method of the invention.

In a particular embodiment, the second and third method of the invention further comprises determining the expression level of at least one additional gene selected from the group consisting of the genes of Table 1.

In a particular embodiment of the second and third method of the invention, the determination of the expression level of the gene is carried out by determining the levels of the mRNA of the gene or by determining the levels of the protein encoded by said gene.

In a particular embodiment of the second and third method of the invention, the TLR-4 agonist is an endotoxin, more particularly lipopolysaccharide (LPS).

In a particular embodiment of the second and third method of the invention, the determination of the expression level of the at least one gene is performed after the blood sample is contacted with the TLR-4 agonist for a period of time between 1 and 3 hours.

In a particular embodiment of the second and third method of the invention, the blood sample that is contacted with the TLR-4 agonist is a whole blood sample.

In a particular embodiment of the second and third method of the invention, the anticoagulant is lithium heparin.

In a particular embodiment of the second and third method of the invention, after step (a) the blood sample is separated into cells and plasma, and wherein the determination of the expression level of the at least one gene is carried out by determining the levels of the mRNA of said gene in the cells and/or by determining the levels of the protein encoded by said gene in the plasma.

Methods for Selecting a Subject for a Therapy

In another aspect, the invention relates to an in vitro method, hereinafter the fourth method of the invention, for selecting a subject suffering from systemic inflammatory response syndrome (SIRS) for a therapy with one or more broad spectrum antibiotics, comprising:

(a) contacting a blood sample from the subject with a TLR4 agonist in the presence of an anticoagulant,
(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and
(c) comparing said expression level with a reference value, wherein the subject is selected for said therapy if
a decreased level of TNFα, IL-1b and/or IFN-β compared to the reference value and/or
an increased level of IL-10, CCL2, IL-2, IL-4 and/or VEGF compared to the reference value
is detected.

In another aspect, the invention relates to an in vitro method, hereinafter the fifth method of the invention, for selecting a subject suffering from cystic fibrosis who is not under treatment with an antibiotic for a therapy with one or more broad spectrum antibiotics, or for selecting a subject suffering from cystic fibrosis who is under treatment with an antibiotic for a therapy with a different type of antibiotic or for a therapy with a different dosage of said antibiotic, comprising:

(a) contacting a blood sample from the subject with a TLR4 agonist in the presence of an anticoagulant, (b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist and (c) comparing said expression level with a reference value, wherein the subject is selected for said therapy if a decreased level of TNFα, IL-1b and/or IFN-β compared to the reference value and/or an increased level of IL-10, CCL2, IL-2, IL-4 and/or VEGF compared to the reference value is detected.

All the terms related to the fourth and fifth methods of the invention have been previously defined in connection with the first, second and third methods of the invention. All the particular and preferred embodiment regarding these terms fully apply to the fourth and fifth methods of the invention.

In a particular embodiment, the fourth and fifth methods of the invention further comprise determining the expression level of at least one additional gene selected from the group consisting of the genes of Table 1.

In a particular embodiment of the fourth and fifth methods of the invention, the determination of the expression level of the gene is carried out by determining the levels of the mRNA of the gene or by determining the levels of the protein encoded by said gene.

In a particular embodiment of the fourth and fifth methods of the invention, the TLR-4 agonist is an endotoxin, more particularly lipopolysaccharide (LPS).

In a particular embodiment of the fourth and fifth methods of the invention, the determination of the expression level of the at least one gene is performed after the blood sample is contacted with the TLR-4 agonist for a period of time between 1 and 3 hours.

In a particular embodiment of the fourth and fifth methods of the invention, the blood sample that is contacted with the TLR-4 agonist is a whole blood sample.

In a particular embodiment of the fourth and fifth methods of the invention, the anticoagulant is lithium heparin.

In a particular embodiment of the fourth and fifth methods of the invention, after step (a) the blood sample is separated into cells and plasma, and wherein the determination of the expression level of the at least one gene is carried out by determining the levels of the mRNA of said gene in the cells and/or by determining the levels of the protein encoded by said gene in the plasma.

Methods of Treatment

In addition, the present invention relates to a method for treating a subject suspected of suffering from bacteremia, the method comprising the steps of: determining whether the subject has bacteremia by:

(a) contacting a blood sample from the patient with a TLR4 agonist in the presence of an anticoagulant;

(b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist; and (c) comparing said level with a reference value;

wherein a decreased level of TNFα, IL-1b, IL-17 and/or IFN-β compared to the reference value and/or an increased level of IL-10, CCL2, IL-2, IL-4 and/or VEGF compared to the reference value is indicative of the presence of bacteremia in the subject; and wherein if the subject has bacteremia, then administering one or more broad spectrum antibiotics.

Suitable broad-spectrum antibiotics as well as specific doses for the treatment of bacteremia have already been described within the context of the second method of the invention, and apply equally to the present case.

In a particular embodiment, when the bacteremia is caused by a respiratory infection, the treatment comprises the intravenous administration of ceftriaxone and levofloxacin. In a more particular embodiment, the dose of ceftriaxone is of at least 0.5 g/24 h, at least 0.6 g/24 h, at least 0.7 g/24 h, at least 0.8 g/24 h, at least 0.9 g/24 h or at least 1 g/24, preferably 1 g/24 h. In another more particular embodiment, the dose of levofloxacin is of at least 250 mg/24 h, at least 300 mg/24 h, at least 350 mg/24 h, at least 400 mg/24 h, at least 450 mg/24 h or at least 500 mg/24 h, preferably 500 mg/24. In another more particular embodiment, the dose of ceftriaxone is of at least 0.5 g/24 h, at least 0.6 g/24 h, at least 0.7 g/24 h, at least 0.8 g/24 h, at least 0.9 g/24 h or at least 1 g/24, preferably 1 g/24 h and the dose of levofloxacin is of at least 250 mg/24 h, at least 300 mg/24 h, at least 350 mg/24 h, at least 400 mg/24 h, at least 450 mg/24 h or at least 500 mg/24 h, preferably 500 mg/24 h. In a particular embodiment, ceftriaxone is administered intravenously, or levofloxacin is administered intravenously. Preferably, both ceftriaxone and levofloxacin are administered intravenously.

In another particular embodiment, when the bacteremia is caused by a respiratory infection and the subject is allergic to penicillin the treatment comprises the intravenous administration of levofloxacin. In a particular embodiment, the dose of levofloxacin is of at least 250 mg/24 h, at least 300 mg/24 h, at least 350 mg/24 h, at least 400 mg/24 h, at least 450 mg/24 h or at least 500 mg/24 h, preferably 500 mg/24 h. In a more particular embodiment, the levofloxacin is administered intravenously.

In another particular embodiment, when the bacteremia does not have an identified focus of infection, or when the bacteremia is caused by a urinary of abdominal infection, the treatment comprises the intravenous administration of piperacillin/tazobactam. In a more particular embodiment, the dose of piperacillin/tazobactam is of at least 2 g/8 h, at least 3 g/8 h, at least 4 g/8 h, at least 4 g/8 h, at least 8 g/8 h, preferably 4 g/8 h. In a particular embodiment, the administration of piperacillin/tazobactam is intravenous.

In another particular embodiment, when the bacteremia does not have an identified focus of infection, or when the bacteremia is caused by a urinary of abdominal infection, and the patient is allergic to penicillin, the treatment comprises the intravenous administration aztreonam and teicoplanin. In a more particular embodiment, the dose of aztreonam is of at least 0.5 g/8 h, at least 0.6 g/8 h, at least 0.7 g/8 h, at least 0.8 g/8 h, at least 0.9 g/8 h, at least 1 g/8 h, at least 1.2 g/8 h or at least 1.5 g/8 h, preferably 1 g/8 h. In another more particular embodiment, the dose of teicoplanin is of at least 200 mg/12 h, at least 250 mg/12 h, at least 300 mg/12 h, at least 350 mg/12 h, at least 400 mg 12 h, at least 450 mg/12 h or at least 500 mg/12 h, preferably 400 mg/12 h, and preferably followed by the same dose every 24 h. In an even more particular embodiment, the dose of aztreonam is of at least 0.5 g/8 h, at least 0.6 g/8 h, at least 0.7 g/8 h, at least 0.8 g/8 h, at least 0.9 g/8 h, at least 1 g/8 h, at least 1.2 g/8 h or at least 1.5 g/8 h, preferably 1 g/8 h and the dose of teicoplanin is of at least 200 mg/12 h, at least 250 mg/12 h, at least 300 mg/12 h, at least 350 mg/12 h, at least 400 mg 12 h, at least 450 mg/12 h or at least 500 mg/12 h, preferably 400 mg/12 h, and preferably followed by the same dose every 24 h. In a particular embodiment, aztreonam is administered intravenously. In a particular embodiment, teicoplanin is administered intravenously. Preferably, both aztreonam and teicoplanin are administered intravenously.

The present invention also relates to a method for treating a subject suffering from systemic inflammatory response syndrome (SIRS), the method comprising the steps of:

determining whether the subject suffers from sepsis by:
- (a) contacting a blood sample from the subject with a TLR4 agonist in the presence of an anticoagulant;
- (b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist; and
- (c) comparing said level with a reference value;

wherein
- a decreased level of TNFα, IL-1b, IL-17 and/or IFN-β compared to the reference value and/or
- an increased level of IL-10, CCL2, IL-2, IL-4 and/or VEGF compared to the reference value is indicative of sepsis;

if the subject suffers from sepsis, then administering one or more broad spectrum antibiotics; and if the subject does not suffers from sepsis, then administering a therapy for SIRS.

In relation to this method of treatment, if the subject with SIRS has sepsis, the same particulars regarding the specific broad-spectrum antibiotic therapy mentioned with regard to the previous method of treatment of bacteremia apply to the present embodiment.

If the subject with SIRS does not have sepsis, the subject is administered a therapy for SIRS, in particular a therapy for SIRS that does not comprise the administration of a broad-spectrum antibiotic. An effective therapy for SIRS wherein the therapy does not comprise the administration of a broad-spectrum antibiotic, when the subject does not have sepsis, is dependent on prompt recognition of the condition. The basic principles of initial critical care include ensuring adequate circulation, airway patency, and gas exchange. The interventions required to achieve these goals depend on the specific physiologic state of the patient at the time of presentation. In a particular embodiment the treatment of SIRS comprises the following actions: immediate resuscitation (respiratory and circulatory support); intubation and mechanical ventilation if respiratory insufficiency, dyspnea, persistent hypotension, or poor peripheral perfusion; fluid resuscitation (hypotension and hypoperfusion); Vasopressors (catecholamines) (e.g., norepinephrine). SIRS treatment may also comprise the administration of glucocorticoids (e.g., prednisone or dexamethasone) if there is an increased risk of cerebral edema or insulin-based control of blood glucose levels.

The present invention also relates to a method for treating a subject suffering from cystic fibrosis (CF), the method comprising the steps of:

determining whether the subject has bacterial pulmonary exacerbation by:
- (a) contacting a blood sample from the subject with a TLR4 agonist in the presence of an anticoagulant;
- (b) determining the expression level of at least one gene selected from the group consisting of tumor necrosis factor alpha (TNFα), IL-1b, IL-10, CCL2, interferon beta (IFN-β), IL-17, IL-2, IL-4 and VEGF in the blood sample previously contacted with the TLR4 agonist; and
- (c) comparing said level with a reference value;

wherein
- a decreased level of TNFα, IL-1b, IL-17 and/or IFN-β compared to the reference value and/or
- an increased level of IL-10, CCL2, IL-2, IL-4 and/or VEGF compared to the reference value is indicative of the presence of bacterial pulmonary exacerbation in the subject; and
- if the subject has bacterial pulmonary exacerbation and is not under treatment with an antibiotic, then administering one or more broad spectrum antibiotics; and
- if the subject has bacterial pulmonary exacerbation and is under treatment with an antibiotic, then administering an increased dosage of said antibiotic or administering a different type of antibiotic; and
- if the subject does not have bacterial pulmonary exacerbation, then administering a therapy for cystic fibrosis.

If the subject with CF does not have a bacterial pulmonary exacerbation, the subject is administered a therapy for cystic fibrosis, in a particular a therapy for cystic fibrosis that does not comprise the administration of broad spectrum antibiotic. Suitable therapies for the treatment of a subject suffering from CF without bacterial pulmonary exacerbation include, without limitation:

Mucolytics as a long-term maintenance therapy, non-limiting examples of mucolytics include dornase alfa and N-acetylcysteine.

Hydrator therapy: Hypertonic saline and mannitol as inhaled agents. Hypertonic saline (7%) has been shown to reduce PEX and marginally improve lung function. Mannitol has been introduced more recently and improves lung function. The drug is available as a dry powder formulation thereby reducing treatment time. Both agents act as irritants and require pre-treatment with a bronchodilator and initial tolerability testing.

Macrolides: Whilst not primarily efficacious against *P. aeruginosa*, there is evidence suggesting efficacy if the organism resides in biofilms, which is the case in chronic *P. aeruginosa* infection. Maintenance therapy with azithromycin, clarithromycin, erythromycin or fidaxomicin.

Anti-inflammatory drugs: such as corticosteroids, for example, inhaled steroids such as beclomethasone, budesonide and fluticasone; oral steroids such as prednisolone and dexamethasone; intravenous steroids such as hydrocortisone and methylprednisolone; and nasal steroids such as mometasone, fluticasone, beclomethasone and budesonide; or nonsteroidal anti-inflammatory drugs (NSAIDs) either systemic or inhaled such as ibuprofen and indomethacin, bronchodilators. High dose ibuprofen has been shown to reduce lung function decline in pediatric patients.

CFTR modulator therapy: Ivacaftor, a CFTR potentiatior and Lumacaftor, a corrector of intracellular trafficking of CFTR.

Physiotherapy, an essential to all CF patients. The two most used techniques are conventional positive expiratory pressure (PEP) and high frequency chest wall oscillation. However, the airway clearance technique should therefore be tailored to the individual. Exercise and physical activity should be integral to the overall physiotherapy management suggested for every individual with CF, irrespective of age and disease severity.

Antibiotic therapy. Airway infection in CF can be divided into early, intermittent and chronic infection. If eradication fails and chronic infection with *P. aeruginosa* develops, inhaled antibiotic therapy has proven efficacy to reduce pulmonary exacerbations, improve lung function and respiratory symptoms and is therefore part of standards of care. Inhaled antibiotic therapy should be administered as long-term maintenance therapy with either single agent therapy or alternating therapy. Alternating different antibiotics is also used in patients deteriorating during months off antibiotics.

Also, for severe/recurrent Allergic Bronchopulmonary Aspergillosis (ABPA), a well-characterised complication in CF patients without bacterial pulmonary exacerbation, oral prednisolone plus/minus antifungal therapy may be used.

In a particular embodiment, when there is a pulmonary infection caused by *Pseudomonas aeruginosa*, the treatment of a subject suffering from CF without bacterial pulmonary exacerbation comprises the administration of tobramycin solution for inhalation (TIS) for about 28 days and up to 3 months of a combination of nebulised colistimethate and oral ciprofloxacin.

In another embodiment, the treatment a subject suffering from CF without bacterial exacerbation having chronic *P. aeruginosa* infection comprises the administration of dry powder inhalation of tobramycin (TOBI Podhaler™); Inhaled aztreonam lysine as an alternative; and Colistimethate as a dry powder preparation.

Also, a prophylactic treatment of CF patients with flucloxacillin may be administered for the first years of life to prevent infection with *Staphylococcus aureus*.

In a final stage of the CF disease without bacterial pulmonary exacerbation, bowel surgery, the implantation of a feeding tube to supply nutrition or lung transplantation may be needed.

As mentioned above, when the presence of bacterial pulmonary exacerbation in the subject is confirmed, then, if the subject is not under treatment with an antibiotic, one or more broad spectrum antibiotics are administered; or, if the subject is under treatment with an antibiotic, an increased dosage of said antibiotic or a different type of antibiotic is prescribed.

Types of broad-spectrum antibiotics have already been defined within the context of the second method of the invention and they can also be used in the present method. In addition, the specific treatments mentioned within the context of the method of treatment of a subject suspected of suffering from bacteremia, when the bacteremia is caused by a respiratory infection, will also apply to the present case.

In a particular embodiment, if the subject has bacterial pulmonary exacerbation and is not under treatment with an antibiotic, since the present method allows detecting the infection at an early stage, the treatment comprises oral administration of broad-spectrum antibiotics. In a particular embodiment, if the subject has bacterial pulmonary exacerbation and is not under treatment with an antibiotic, the method does not comprise the intravenous administration of the broad-spectrum antibiotic.

In another particular embodiment, if the subject has bacterial pulmonary exacerbation and is under treatment with an antibiotic, the treatment comprises the increment of the antibiotic dose or the modification of the specific antibiotic. In a particular embodiment, if the subject has bacterial pulmonary exacerbation and is under treatment with an antibiotic, the treatment comprises oral administration of broad-spectrum antibiotics. In a particular embodiment, if the subject has bacterial pulmonary exacerbation and is under treatment with an antibiotic, the method does not comprise the intravenous administration of the broad-spectrum antibiotic.

In some embodiments, when bacterial pulmonary exacerbation is confirmed, since the disclosed method allows early detection of an infection, oral administration of antibiotics is preferred. In another embodiment, when the method is applied to a subject with persistent bacterial infection, the therapy will comprise the administration of intravenous antibiotics and possibly, the monitoring of the subject in an intensive care unit.

In a particular embodiment, when bacterial pulmonary exacerbation is confirmed, the treatment will comprise intravenous antibody treatment, bronchodilators and corticosteroids for 14 days. Simultaneous use of inhaled and intravenous antibiotics may be prescribed.

In a particular embodiment, when the bacterial pulmonary exacerbation is caused by *P. aeruginosa*, known to by a MDR (multidrug resistant bacteria), the treatment may comprise the use of 2 combined antibiotics, one selected from polymyxin B or ceftazidime and one of tazobactam, piperacillin, ceftazidime, cefepime, other oxy-imino-lactams, imipenem and meropenem, aminoglycosides, quinolones, fluoroquinolones carbapenems and antipseudomonal penicillin and cephalosporins. If this approach does not give the expected results, a change of antibiotics and/or increase the doses may be prescribed. Although, if the microbiological analysis (and the antibiotic sensitivity test results) of the patient is known the treatment will be focused to target the specific pathogen bacteria. In another embodiment, when the bacterial pulmonary exacerbation is caused by *Klebsiella, Enterobacter*, and *Serratia* species, carbapenems may be used.

In another embodiment, when the bacterial pulmonary exacerbation is caused by *Acinetobacter* species, *Stenotrophomonas maltophilia*, and *Burkholderia cepacian*, the antibiotic may be selected from carbapenems, sulbactam, rimethoprim-sulfamethoxazole, ticarcillin-clavulanate, or a fluoroquinolone and ceftazidime.

In another embodiment, when the bacterial pulmonary exacerbation is caused by Methicillin-resistant *Staphylococcus aureus*, linezolid, vancomycin may be administered.

In another embodiment, when the bacterial pulmonary exacerbation is caused by *Streptococcus pneumoniae* and *Haemophilus influenzae*: vancomycin, linezolid, or broad-spectrum quinolones may be used.

The CF patients should continue receiving the maintenance treatment for the lung function during a pulmonary exacerbation. The airway clearance treatment should be increased during a pulmonary exacerbation.

In a particular embodiment, the method for treating a subject suspected of suffering from bacteremia, the method for treating a subject suffering from systemic inflammatory response syndrome (SIRS) and the method for treating a subject suffering from cystic fibrosis comprises a step of obtaining the blood sample from the subject before step (a).

In a particular embodiment, within the context of the method for treating a subject suspected of suffering from bacteremia, the method for treating a subject suffering from systemic inflammatory response syndrome (SIRS) and the method for treating a subject suffering from cystic fibrosis, the subject diagnosed with bacteremia, sepsis or bacterial pulmonary exacerbation, experience a health improvement or amelioration of the symptoms within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours after the collection of the blood sample.

All the terms related to the method for treating a subject suspected of suffering from bacteremia, the method for treating a subject suffering from systemic inflammatory response syndrome (SIRS) and the method for treating a subject suffering from cystic fibrosis have been previously defined in connection with the first, second, third, fourth and fifth methods of the invention. All the particular and preferred embodiment regarding these terms fully apply to the method for treating a subject suspected of suffering from bacteremia, the method for treating a subject suffering from systemic inflammatory response syndrome (SIRS) and the method for treating a subject suffering from cystic fibrosis.

In a particular embodiment, the method for treating a subject suspected of suffering from bacteremia, the method for treating a subject suffering from systemic inflammatory response syndrome (SIRS) and the method for treating a subject suffering from cystic fibrosis further comprise determining the expression level of at least one additional gene selected from the group consisting of the genes of Table 1.

In a particular embodiment, within the context of the method for treating a subject suspected of suffering from bacteremia, the method for treating a subject suffering from systemic inflammatory response syndrome (SIRS) and the method for treating a subject suffering from cystic fibrosis, the determination of the expression level of the gene is carried out by determining the levels of the mRNA of the gene or by determining the levels of the protein encoded by said gene.

In a particular embodiment, within the context of the method for treating a subject suspected of suffering from bacteremia, the method for treating a subject suffering from systemic inflammatory response syndrome (SIRS) and the method for treating a subject suffering from cystic fibrosis, the TLR-4 agonist is an endotoxin, more particularly lipopolysaccharide (LPS).

In a particular embodiment of the method for treating a subject suspected of suffering from bacteremia, the method for treating a subject suffering from systemic inflammatory response syndrome (SIRS) and the method for treating a subject suffering from cystic fibrosis, the determination of the expression level of the at least one gene is performed after the blood sample is contacted with the TLR-4 agonist for a period of time between 1 and 3 hours.

In a particular embodiment of the method for treating a subject suspected of suffering from bacteremia, the method for treating a subject suffering from systemic inflammatory response syndrome (SIRS) and the method for treating a subject suffering from cystic fibrosis, the blood sample that is contacted with the TLR-4 agonist is a whole blood sample.

In a particular embodiment of the method for treating a subject suspected of suffering from bacteremia, the method for treating a subject suffering from systemic inflammatory response syndrome (SIRS) and the method for treating a subject suffering from cystic fibrosis, the anticoagulant is lithium heparin.

In a particular embodiment of the method for treating a subject suspected of suffering from bacteremia, the method for treating a subject suffering from systemic inflammatory response syndrome (SIRS) and the method for treating a subject suffering from cystic fibrosis, after step (a) the blood sample is separated into cells and plasma, and wherein the determination of the expression level of the at least one gene is carried out by determining the levels of the mRNA of said gene in the cells and/or by determining the levels of the protein encoded by said gene in the plasma.

In a particular embodiment, within the context of the method for treating a subject suspected of suffering from bacteremia, the method for treating a subject suffering from systemic inflammatory response syndrome (SIRS) and the method for treating a subject suffering from cystic fibrosis, the administration of a therapy is commenced within less than 24 hours, suitable within 22 hours, within 20 hours, within 18 hours, within 16 hours, within 14 hours, within 12 hours, within 20 hours, within 18 hours, within 16 hours, within 14 hours, within 12 hours, within 10 hours, within 8 hours, within 6 hours, within five hours, suitably within four hours, suitably within three hours following obtaining said blood sample.

In another embodiment, within the context of the method for treating a subject suspected of suffering from bacteremia, the method for treating a subject suffering from systemic inflammatory response syndrome (SIRS) and the method for treating a subject suffering from cystic fibrosis, the prognosis of the subject having bacteremia or an infection is improved compared to the prognosis of a subject who has commenced treatment for bacteremia or an infection following diagnosis by positive blood culture.

In another embodiment, within the context of the method for treating a subject suspected of suffering from bacteremia, the method for treating a subject suffering from systemic inflammatory response syndrome (SIRS) and the method for treating a subject suffering from cystic fibrosis, the determination of whether the patient has bacteremia, sepsis or bacterial pulmonary exacerbation comprises:

(a) determining the expression level of at least one gene selected from the group consisting of tumor necrosis factor alpha (TNFα), IL-1b, IL-10 and CCL2, in the blood sample previously contacted with the TLR4 agonist; and (b) comparing said level with a reference value.

In another embodiment, within the context of the method for treating a subject suspected of suffering from bacteremia, the method for treating a subject suffering from systemic inflammatory response syndrome (SIRS) and the method for treating a subject suffering from cystic fibrosis, determining whether the patient has bacteremia, sepsis or bacterial pulmonary exacerbation further comprises:

(a) determining the expression level of at least one gene selected from the group consisting of the genes of Table 1, in the blood sample previously contacted with the TLR4 agonist; and (b) comparing said level with a reference value;

wherein an increased or decreased level compared to the reference value is indicative of the presence of bacteremia or an infection in the subject.

In a further embodiment, within the context of the method for treating a subject suspected of suffering from bacteremia, the method for treating a subject suffering from systemic inflammatory response syndrome (SIRS) and the method for treating a subject suffering from cystic fibrosis, before step (a) the blood sample is separated into cells and plasma, and the determination of the expression level of the at least one gene is carried out by determining the level of the mRNA of said gene in the cells.

In a further embodiment, within the context of the method for treating a subject suspected of suffering from bacteremia, the method for treating a subject suffering from systemic inflammatory response syndrome (SIRS) and the method for treating a subject suffering from cystic fibrosis before step (a) the blood sample is separated into cells and plasma, and the determination of the expression level of the at least one gene is carried out by determining the level of the protein encoded by said gene in the plasma.

The term TLR4 agonist has been defined within the context of the first method of the invention and applies equally to the present case.

In a particular embodiment, the TLR4 agonist is not an endotoxin. In another embodiment, the TLR4 agonist is a non-naturally occurring agonist such as the ones previously described.

Kit of the Invention and its Uses

In another aspect, the invention relates to a kit comprising a reagent specific for determining the level of expression of at least one cytokine selected from the group consisting of tumor necrosis factor alpha (TNF-α), IL-1b, IL-10, CCL2, interferon beta (IFN-β), IL-17, IL-2, IL-4, and VEGF, further comprising a TLR4 agonist. In general the present invention is directed to a diagnostic kit that provides an integrated system for detecting the presence or absence as well as the expression levels of one or more genes of interest or the product of the expression of said genes within a test sample, over a broad range of possible concentrations of the one or more genes of interest or the expression product thereof. Means for determining the expression level of a gene or a product of expression of said genes have been described within the context of the method for detecting bacteremia of the invention and apply equally to the kit of the invention. Therefore, the present kit may include essential elements required for measuring or quantifying mRNA, such the ones for performing RT-PCR, like primers specific for each marker gene or for control sequences, deoxynucleotides, enzymes such as Taq-polymerase and reverse transcriptase, DNAse, RNAse inhibitor, DEC-treated water, sterile water. The kit may also include essential elements for measuring the expression levels of the cytokines of interest in which the amount of protein is measured using antibodies specifically binding to the cytokines of interest and other means for analysis methods such as western blot, enzyme linked immunosorbent assay (ELISA), enzyme linked oligonucleotide assay (ELONA), ELONA-RT qPCR, radioimmunoassay (RIA), radioimmunodiffusion, Ouchterlony immunodiffusion, rocket Immunoelectrophoresis, immunohistostaining, immunoprecipitation assay, complement fixation assay, FACS, and protein chip assay.

In some embodiments, the quantity and/or expression of the one or more genes of interest are also detected in a quantitative assay. The diagnostic kit may employ a lateral flow assay device and a separate insert and one or more assay reagents for detecting the expression level of one of more genes of interest within the test sample. The assay reagents include affinity molecule(s) tagged with detection probes that are capable of producing a detection signal representing the presence or expression level of the one or more genes of interest or expression products thereof in the test sample. One way of quantifying one or more of the gene of interest is by preparing suitable standard curves using known concentrations of the one or more genes of interest or expression products thereof.

As used herein, the term "reagent specific for determining the expression level" means a reagent used to detect the expression of one or more genes (e.g. a cytokine of interest), including, but not limited to nucleic acid probes capable of specifically hybridizing to a gene of interest, a PCR primer capable of specifically amplifying the gene of interest, a PCR primer capable of specifically amplifying the gene of interest, antibodies of aptamers capable of specifically binding to the expression product of the gene of interest.

The kit further comprises a TLR-4 agonist.

Suitable TLR-4 agonists have been described within the context of the in vitro detection method of the invention and are also applicable to the kit of the invention. In a particular embodiment, the TLR-4 agonist is an endotoxin. In a preferred embodiment, the TLR-4 agonist is LPS. In another embodiment, the TLR-4 agonist is a non-natural occurring agonist such as the ones described within the context of the in vitro method for detecting bacteremia.

Specific genes of interest or expression products thereof may include one or more selected from the list consisting of: tumour necrosis factor alpha (TNF-α), IL-1b, IL-10, CCL2, interferon beta (IFN-β), IL-17, IL-2, IL-4, and VEGF. The kit of the invention comprises at least one reagent specific for determining the expression level of one of the cytokines of interest. Thus in an embodiment, the kit of the invention comprises a reagent specific for determining the expression level of one of the cytokines selected from TNF-α, IL-1β, IL-10 or CCL2. In another embodiment, the kit of the invention comprises reagents specific for determining the expression level of TNF-α and one or more of the cytokines selected from IL-1β, IL-10 or CCL2.

Additional combinations of reagents specific for determining the expression level of the cytokines of interest comprise the combinations specified within the context of the in vitro method for detecting bacteremia.

In a preferred embodiment, the kit comprises a reagent specific for determining the expression level of TNF-α.

In a particular embodiment, the reagents specific for determining the expression level of at least one of the specific genes comprises at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least, 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least, 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90% of the total of the reagents of the kit. In a particular embodiment, the reagents specific for determining the expression level of at least one gene comprise reagent specific for determining the expression level of at least one gene from the group consisting of tumour necrosis factor alpha (TNFα), IL-1b, IL-10, CCL2, interferon beta (IFN-β), IL-17, IL-2, IL-4 and VEGF. In another particular embodiment, the reagents specific for determining the expression level of at least one gene comprise reagent specific for determining the expression level of at least one gene selected from the group of genes of Table 1.

In another embodiment, the kit of the invention further comprises a RPMI (Roswell Park Memorial Institute) or DMEM (Dulbecco's modified Eagle's medium) culture medium.

Suitable culture mediums for the kit of the invention include without limitation.

In another embodiment, the kit of the invention further comprises a reagent specific for determining the expression level of at least one additional cytokine selected from the group consisting of the cytokines of Table 1.

In another embodiment, the kit further comprises an anticoagulant. In a preferred embodiment, the anticoagulant is lithium heparin.

In another embodiment, the reagent specific for determining the expression level of at least one cytokine is an antibody that specifically binds to the protein encoded by said gene.

As used herein, the term "antibody" relates to a monomeric or multimeric protein that comprises at least one polypeptide having the capacity for binding to a determined antigen, or epitope within the antigen, and comprising all or part of the light or heavy The term antibody also includes any type of known antibody, such as, for example, polyclonal antibodies, monoclonal antibodies and genetically engineered antibodies, such as chimeric antibodies, humanized antibodies, primatized antibodies, human antibodies and bispecific antibodies (including diabodies), multispecific antibodies (e.g. bispecific antibodies), and antibody fragments so long as they exhibit the desired biological activity.

The invention also comprises the use of fragments of the different types of antibodies mentioned above which substantially preserve the anti-angiogenic activity of the antibody. The term "antibody fragment" includes antibody fragments such as Fab, F(ab')2, Fab', single chain Fv fragments (scFv), diabodies and nanobodies.

In general, the use of antibodies involves contacting a sample containing or suspected of containing an increased or decreased expression level of the cytokine of interest with at least one antibody that specifically binds to the expressed cytokine. A signal is then generated indicative of the presence or amount of complexes formed by the binding of polypeptides in the sample to the antibody. The signal is then related to the presence or amount of the expressed cytokine in the sample. Numerous methods and devices are well known to the skilled artisan for the detection and analysis of expressed proteins. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994.

The assay devices and methods known in the art can utilize labelled molecules in various sandwich, competitive, or non-competitive assay formats, to generate a signal that is related to the presence or amount of the expressed cytokines of interest. Suitable assay formats also include chromatographic, mass spectrographic, and protein "blotting" methods. Additionally, certain methods and devices, such as biosensors and optical immunoassays, may be employed to determine the presence or amount of the expressed cytokines without the need for a labelled molecule. See, e.g., U.S. Pat. Nos. 5,631,171; and 5,955,377. One skilled in the art also recognizes that robotic instrumentation including but not limited to Beckman ACCESS®, Abbott AXSYM®, Roche ELECSYS®, Dade Behring STRATUS® systems are among the immunoassay analysers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a coloured spot. Antibodies or other polypeptides may be bound to specific zones of assay devices either by conjugating directly to an assay device surface, or by indirect binding. In an example of the lateral flow, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components, such an antibody, in the sample being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dinitrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the kit comprises reagents for the analysis of the expression levels of at least one of the expressed cytokines which comprise at least one antibody that specifically binds to the expressed cytokine. The kit can also include devices and instructions for performing one or more of the diagnostic correlations described herein. Preferred kits will comprise an antibody pair for performing a sandwich assay, or a labelled species for performing a competitive assay, for the expressed cytokine. Preferably, an antibody pair comprises a first antibody conjugated to a solid phase and a second antibody conjugated to a detectable label. Each of the antibodies may be monoclonal antibodies, or polyclonal antibodies. In another embodiment one of the pair antibodies is monoclonal whereas the other is polyclonal. The instructions for use of the kit and performing the correlations can be in the form of labelling, which refers to any written or recorded material that is attached to, or otherwise accompanies a kit at any time during its manufacture, transport, sale or use. For example, the term labelling encompasses advertising leaflets and brochures, packaging materials, instructions, audio or video cassettes, computer discs, as well as writing imprinted directly on kits.

In certain embodiments, the assay is performed using a single-use disposable test device. Such test devices often take the form of lateral flow devices which are now familiar from the common use of over-the-counter pregnancy tests.

Thus, in a preferred embodiment, the reagent specific for determining the level of at least one cytokine is immobilized on a lateral flow device.

The term "lateral flow" as used herein refers to flow of reagents in a longitudinal direction through a substantially flat porous material. Such porous material is "substantially flat" if the thickness of the material is no more than 10% of the length and width dimensions.

Generally, these assay devices have an extended base layer on which a differentiation can be made between a sample addition region and an evaluation region. In typical use, the sample is applied to the sample addition region, flows along a liquid transport path which runs parallel to the base layer, and then flows into the evaluation region. A capture reagent is present in the evaluation region, and the captured protein can be detected by a variety of protocols to detect visible moieties associated with the captured protein. For example, the assay may produce a visual signal, such as colour change, fluorescence, luminescence, and the like, when indicating the presence or absence of a protein in a biological sample.

A sample addition region can be provided, for example, in the form of an open chamber in a housing; in the form of an absorbent pad; etc. The sample addition region can be a port of various configurations, that is, round, oblong, square and the like or the region can be a trough in the device.

In a particular embodiment, the sample addition region is provided with a TLR-4 agonist. In another embodiment, the sample addition region is provided with a TLR-4 agonist and an anticoagulant. In a preferred embodiment the TLR-4 agonist is LPS. In another embodiment the TLR-4 agonist is a non-naturally occurring agonist.

In another embodiment, the sample addition regions is provided with culture medium. In another embodiment, the sample addition region comprises a culture medium and a TLR-4 agonist and optionally, and anticoagulant. In another embodiment, the sample addition region comprises an anticoagulant, culture medium and a TLR-4 agonist. In a particular embodiment the anticoagulant is lithium heparin.

In another embodiment, the capture reagent in the evaluation region comprises any antibody or aptamer capable of binding to any of the cytokines of the invention.

A filter element can be placed in, on, or adjacent to the sample addition region to filter particulates from the sample, such as to remove or retard blood cells from blood so that plasma can further travel through the device. Filtrate can then move into a porous member fluidly connected to the filter. Suitable filters for removing or retarding cellular material present in blood are well known in the art. See, e.g., U.S. Pat. Nos. 4,477,575; 5,166,051; 6,391,265; and 7,125,493, each of which is hereby incorporated by reference in its entirety. Many suitable materials are known to skilled artisans, and can include glass fibers, synthetic resin fibers, membranes of various types including asymmetric membrane filters in which the pore size varies from about 65 to about 15 pm, and combinations of such materials. In addition, a filter element can comprise one or more chemical substances to facilitate separation of red blood cells from blood plasma.

Examples of such chemical substances are thrombin, lectins, cationic polymers, antibodies against one or more red blood cell surface antigens and the like. Such chemical substance(s) which facilitate separation of red blood cells from plasma may be provided in the filter element by covalent means, nonspecific absorption, etc.

In certain embodiments, a label zone is located downstream of the sample receiving zone, and contains a diffusively located labelled reagent that binds to the cytokine or protein of interest or that competes with the cytokine or protein of interest for binding to a binding species. Alternatively, the label zone can be eliminated if the labelled reagent is premixed with the sample prior to application to the sample receiving zone. A detection zone is disposed downstream of from the label zone, and contains an immobilized capture reagent that binds to the cytokine or protein of interest.

In a particular embodiment, the reagent specific for determining the expression levels of the cytokines of interest is an antibody or/and aptamer. It is understood that the membrane may comprise one or several reagents specific for determining the expression levels of the cytokines of interest. Thus, in a preferred embodiment, the membrane comprises reagents specific for determining the expression levels of any of tumour necrosis factor alpha (TNFα), IL-1b, IL-10, CCL2, interferon beta (IFN-β), IL-17, IL-2, IL-4 and VEGF. In The device may further comprise various control locations which are read to determine that the test device has been run properly. By way of example, a procedural control zone may be provided separate from the assay detection zone to verify that the sample flow is as expected. The control zone is preferably a spatially distinct region at which a signal may be generated that is indicative of the proper flow of reagents. The procedural control zone may contain the cytokine or protein of interest, or a fragment thereof, to which excess labelled antibody used in the assay can bind. In operation, a labelled reagent binds to the control zone, even when the cytokine or protein of interest is absent from the test sample. The use of a control line is helpful in that appearance of a signal in the control line indicates the time at which the test result can be read, even for a negative result.

Thus, when the expected signal appears in the control line, the presence or absence of a signal in the capture zone can be noted. The device may further comprise a negative control area. The purpose of this control area is to alert the user that the test device is not working properly. When working properly, no signal or mark should be visible in the negative control area.

The outer casing or housing of such an assay device may take various forms. Typically, it will include an elongate casing and may have a plurality of interfitting parts. In a particularly preferred embodiment, the housing includes a top cover and a bottom support. The top cover contains an application aperture and an observation port. In a preferred embodiment, the housing is made of moisture impervious solid material, for example, a plastic material. It is contemplated that a variety of commercially available plastics, including, but not limited to, vinyl, nylon, polyvinyl chloride, polypropylene, polystyrene, polyethylene, polycarbonates, polysulfanes, polyesters, urethanes, and epoxies maybe used to construct a housing.

If necessary, the colorimetric, luminescent, or fluorescent intensity of the detectable label being employed may be then evaluated with an instrument that is appropriate to the label. By way of example, a fluorimeter can be used to detect fluorescent labels; a reflectometer can be used to detect labels that absorb light, etc.

The concentration of the cytokine or protein of interest in the samples may be determined by correlating the measured response to the amount of cytokine or protein in the sample fluid.

Measures of test accuracy may be obtained as described in Fischer et ah, Intensive Care Med. 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(I-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

In another embodiment, the kit of the invention further comprises an anticoagulant.

In a particular embodiment, the anticoagulant is lithium heparin.

Figure 8:
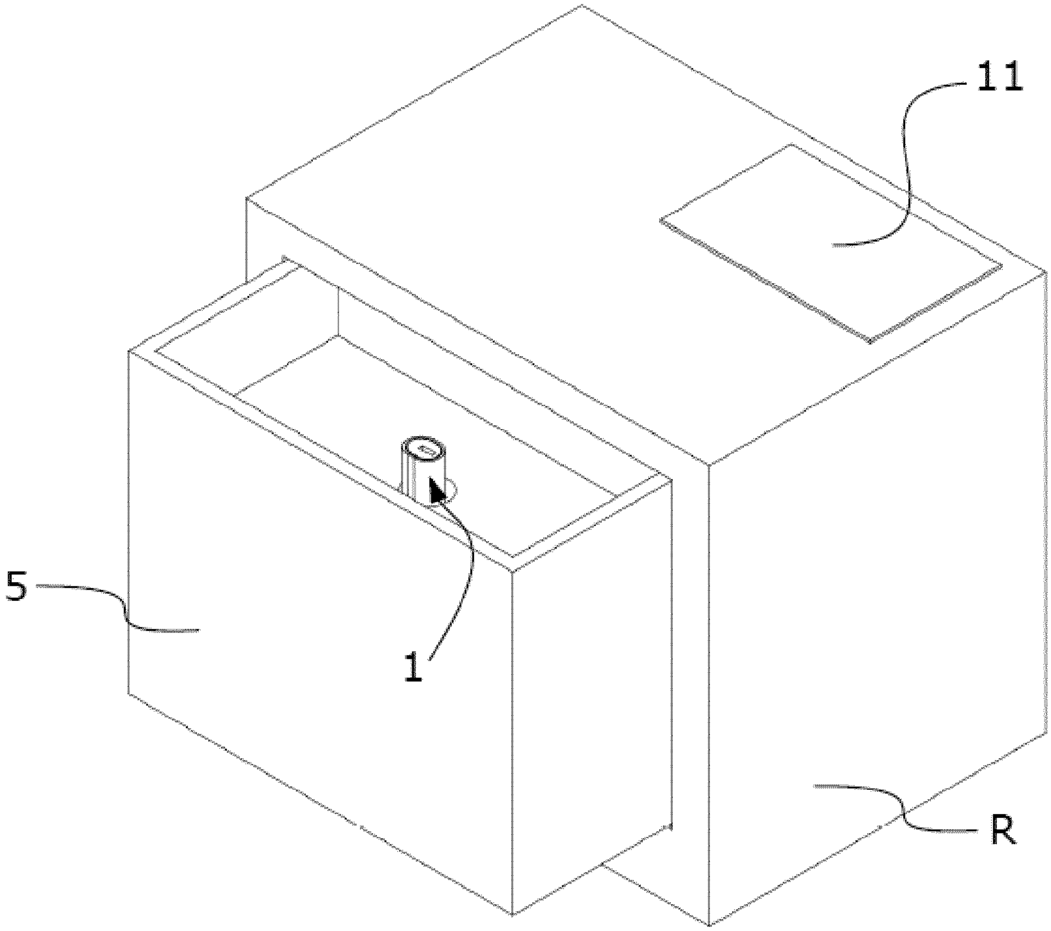
FIG. 8 shows a perspective view of an embodiment of the assembly present in the kit of the sixth aspect of the invention when performing the method of the eighth aspect of the invention in a reader.

In a particular embodiment, the kit comprises an assembly (1), being said assembly (1) configured for being housed inside a drawer (5) of a reader (R), as the one shown in FIG. 8. The assembly (1) is configured as a cassette, by means of several tubes which cooperate together in order to establish a fluid communication which allows the analysis of a blood sample when housed in the mentioned reader (R).

Figure 4:
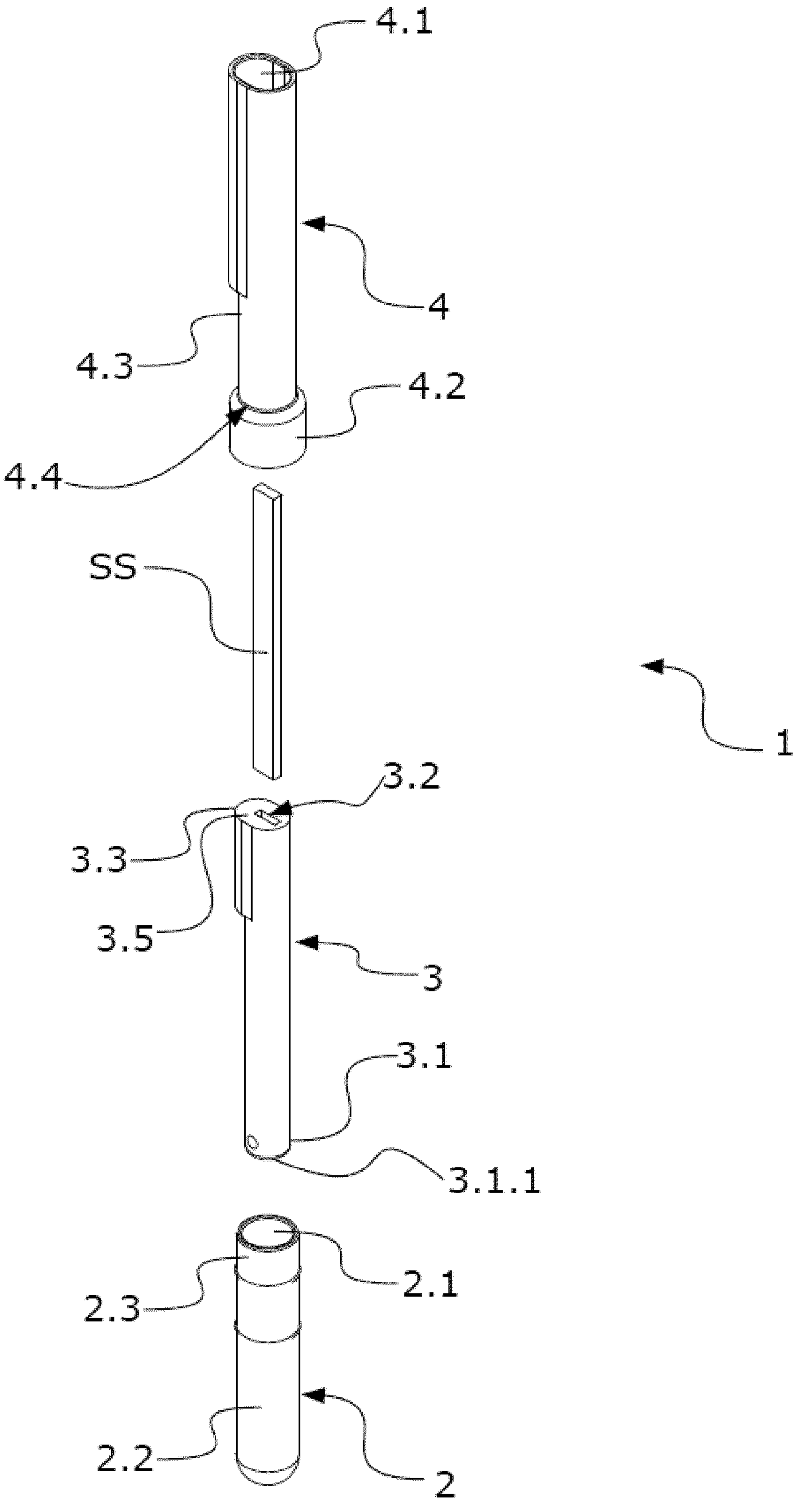
FIG. 4 shows an exploded view according to an embodiment of the assembly present in the kit of the sixth aspect of the invention.

Particularly, FIG. 4 shows an exploded view of the assembly (1) or individual cassette.

The assembly (1) comprises a second tube (3), which extends along a longitudinal direction X-X', wherein one of its ends is a guided end (3.1) and comprises a hole (3.1.1). This second tube (3) also comprises a second chamber (3.2) which can be reached through the hole (3.1.1).

Said second chamber (3.2) contains a porous solid support (SS), such as a lateral flow strip, which has one or more antibodies immobilized on it, said one or more antibodies specifically binding to the protein encoded by the gene already mentioned. The lateral flow strip is covering an extended area of the inner surface of the second chamber (3.2).

The porous solid support can be any suitable material through which the sample can flow by capillary, such as porous paper, nitrocellulose, microstructured polymers or sintered polymers. The antibody is immobilized on this solid support either by conjugating directly to an assay device surface, or by indirect binding, for example, the antibody may be immobilized on particles that are immobilized to the surface of the solid support.

The end of the second tube (3), opposite to the guided end (3.1), is a receiving end (3.3) wherein a pressing area (3.5) is configured. This pressing area (3.5) is able to receive an external tool which transmits a pressure to the second tube (3), said external pressure causing a movement of the second tube (3) along the longitudinal direction X-X'.

FIG. 4 also shows a first hollow tube (2), which extends along the defined longitudinal direction X-X', and wherein one of its ends, according to said longitudinal direction X-X', is an open end (2.1). The hollow tube (2) also comprises a first chamber (2.2), which is accessible through the open end (2.1).

The blood sample to be analysed is housed inside the first chamber (2.2), introduced in it through the open end (2.1). A TLR4 agonist is also housed inside the first chamber (2.2).

The assembly (1) shown in FIG. 4 also comprises a connection tube (4) which also extends along the longitudinal direction X-X'. Said connection tube (4) is able to connect both the first hollow tube (2) and the second tube (3), and is coupled with the hollow tube (2), both tubes (2, 4) being coaxial when coupled.

Particularly, as shown in FIG. 4, the connection tube (4) comprises a guiding end (4.1), in correspondence with the second tube (3) and through which said second tube (3) is introduced inside the connection (4), thus both tubes (3, 4) being also coaxial. The connection tube (4) also comprises a connection end (4.2), opposite to the guiding end (4.1), the connection end (4.2) being in correspondence with the hollow tube (2).

It can also be observed in FIG. 4 a foil (4.4) or membrane, located at the connection end (4.2) of said connection tube (4), particularly at the beginning of the screw performed at said connection end (4.2) as shown in FIG. 4, which blocks the communication between the first hollow tube (2) and the second tube (3) through its hole (3.1.1) without blocking the connection provided for being coupled with the first hollow tube. Particularly, the mentioned foil (4.4) blocks the access into the second chamber (3.2) of the blood sample present in the first chamber (2.2) of the first hollow tube (2). Said foil (4.4) can be teared up or broken in order to allow the access of the second tube (3.2), particularly of the guided end (3.1) of said second tube (3) into the first chamber (2.2) thus giving the blood sample access to the second chamber (3.2) of the second tube (3). Said tearing of the foil (4.4) is produced either by external means or by exerting a pressure on said foil (4.4) by means of the guided end (3.1) of the second tube (3) when said tube (3) slides inside the connection tube (4).

The connection tube (4) and the hollow tube (2) are fixed by corresponding coupling means.

Particularly, the hollow tube (2) shows in the present embodiment a screwed area (2.3) at the open end (2.1), particularly embodied in the outer surface of the open end (2.1). Said screwed area (2.3) corresponds with a complementary screwed area (4.2.1) such that both screwed areas (2.3, 4.2.1) can be coupled together in order to detachably fix the connection tube (4) and the first hollow tube (3).

Thus, when mounted, in an operative position, the second tube (3) is housed inside the connection tube (4) and is able to move along the longitudinal direction X-X' inside said connection tube (4), whilst the first hollow tube (2) is fixed to said connection tube (4) and does not allow any movement once coupled.

In order to be able to analyse the blood sample, such blood sample needs to reach the lateral flow strip (SS) housed inside the second chamber (3.2) of the second tube (3).

Therefore, as shown in FIG. 4, the second tube (3) moves along the longitudinal direction X-X', inside the connection tube (4), being partially introduced inside the first chamber (2.2) of the first hollow tube (2). The guided end (3.1) thus reaches the blood sample housed in the first chamber (2.2), and said blood sample enters through the hole (3.1.1) into the second chamber (3.2), reaching the lateral flow strip (SS).

Figure 5A:
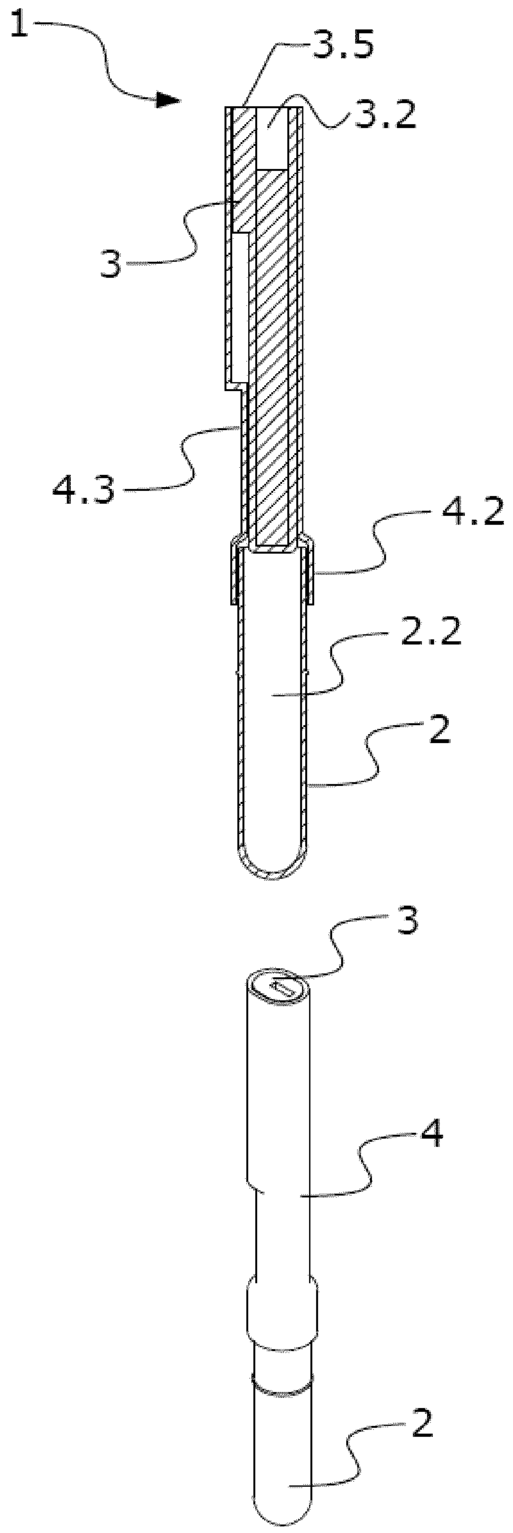
FIGS. 5A and 5*b* show, respectively, a perspective view of the assembly and the assembly once coupled according to the embodiment of the assembly of FIG. 4.
Figure 5B:
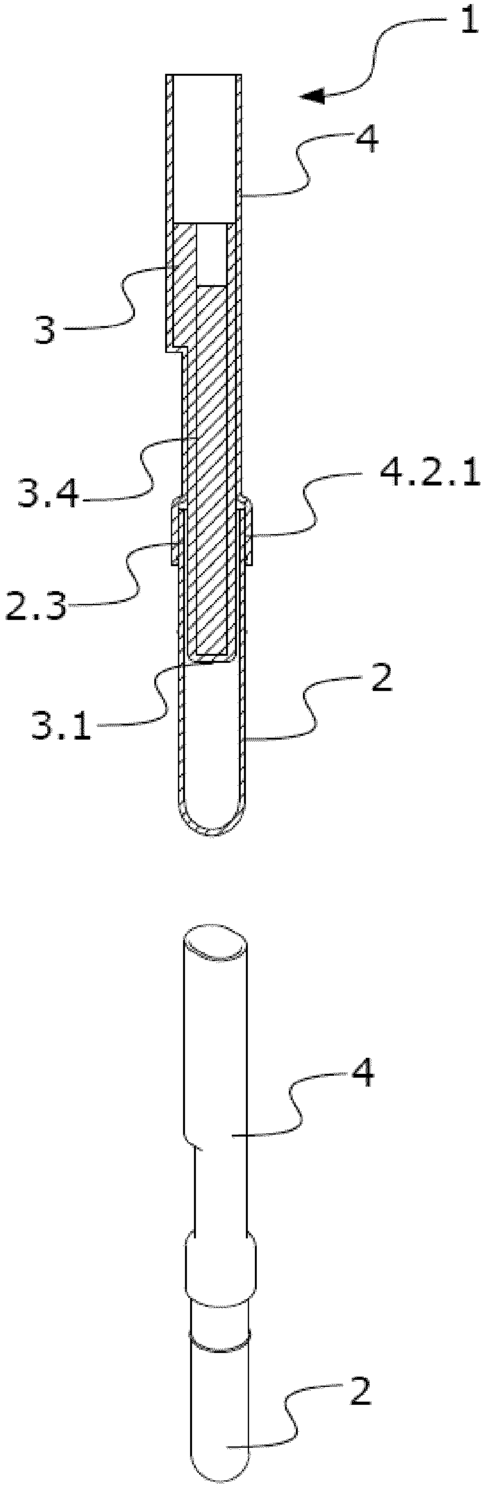

FIGS. 5A and 5B show the movement of said second tube (3) inside the connection tube (4) to reach the first chamber (2.2).

Particularly, FIG. 5A shows the connection tube (4) screwed to the first hollow tube (2), and the second tube (3) housed inside the connection tube (3) in a first position when being mounted in its operative mode.

In this first position, it can be observed that the guided end (3.1) of the second tube (3) is not introduced inside the first chamber (2.2), and thus the blood sample housed inside said first chamber (2.2) cannot reach the lateral flow strip (SS) present in the second chamber (3.2).

FIG. 5B shows the same configuration, wherein the connection tube (4) screwed to the first hollow tube (2), and the second tube (3) housed inside the connection tube (3) in a second position when being mounted in its operative mode.

This second position provides the fluid communication between the first (2.2) and second (3.2) chambers, wherein the blood sample leaves the first chamber (2.2) to reach the lateral flow strip (SS). The second position is achieved after the longitudinal movement of the second tube (3) along the longitudinal direction X-X', inside the connection tube (4).

In order to pass a determined amount of blood sample to the lateral flow strip (SS), the foil (4.4) is teared up, and the blood sample passively enters into the second chamber (3.2) through the hole (3.1.1) as mentioned, movement of the blood sample caused only by the contact of the second tube (3), particularly of its guided end (3.1) with the blood sample present in the first chamber (2.2).

Once the blood sample has reached the lateral flow strip (SS), it progresses along said lateral flow strip (SS) due to capillarity, reaching the point wherein the antigens are present, providing a result in a reading area (3.4) which can be read by external means, such as a sensor (S).

In both first and second positions, the first hollow tube (2), the second tube (3) and the connection tube (4) are coaxial.

Additionally, although not shown in FIG. 5B, the second position of the assembly (1) is achieved after applying an external pressure with an external tool on the pressing area (3.5) of the second tube (3).

FIGS. 5A and 5B also show the mentioned reading area (3.4) located at the lateral surface of the second tube (3), which allows the access of an external sensor (S) to measure the result shown by the porous solid support (SS).

FIGS. 5A and 5B also show a recessed area (4.3) present in the lateral surface of the connection tube (4), embodied as a hole in said tube.

It can be observed how in the first position of the assembly, in FIG. 5A, the recessed area (4.3) allows reaching the lateral surface of the second tube (3). However, it is in the second position of the assembly, as shown in FIG. 5B, where the reading area (3.4) and the recessed area (4.3) are located in correspondence. In said position, the external sensor reaches the reading area (3.4) through the hole of the connection tube (4), configured as the recessed area (4.3) which completely fits with the reading area (3.4).

Figure 6:
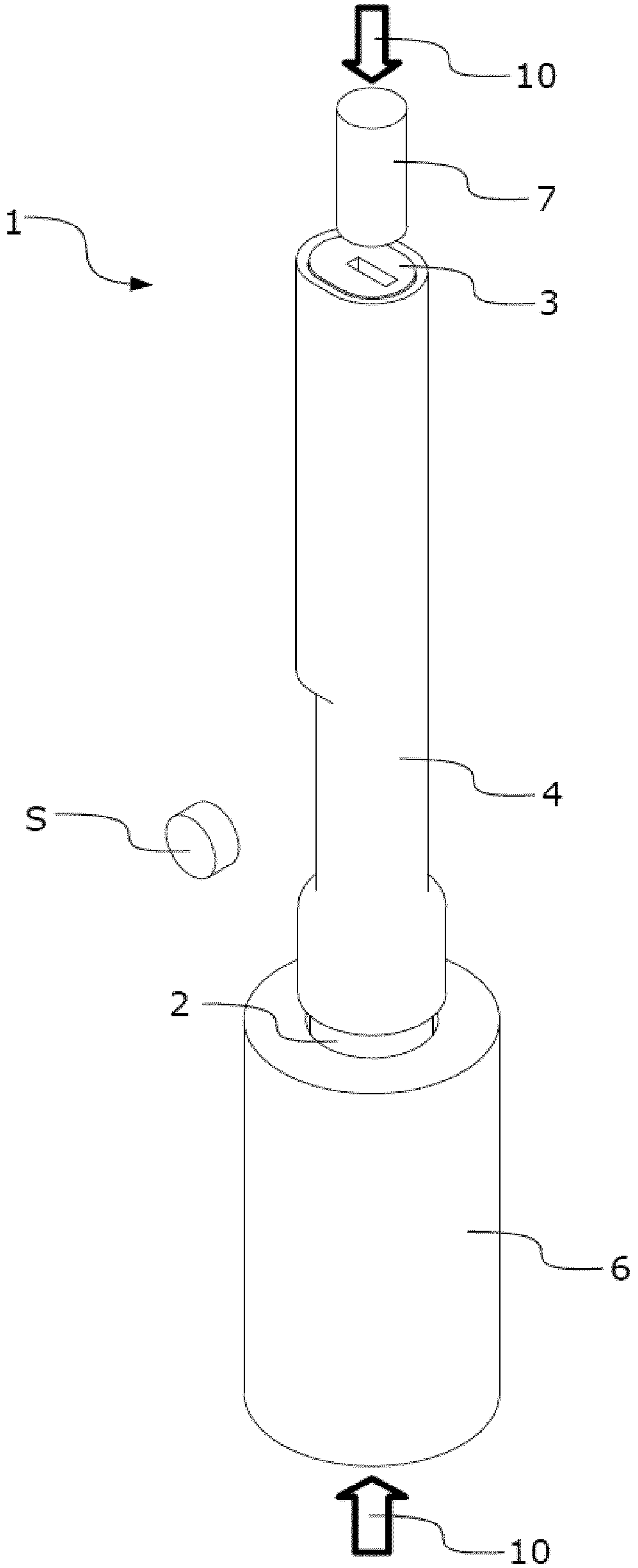
FIG. 6 shows a perspective view of another embodiment of the assembly present in the kit of the sixth aspect of the invention when performing the method of the eighth aspect of the invention.

FIG. 6 shows the first position of the assembly (1), the same as the one shown in FIG. 5A, the assembly (1) being prepared to change to its second position (as shown in FIG. 5B).

Particularly, external tools (6, 7) embodied as actuators, are shown, respectively, in contact with the first hollow tube (2) and with the pressing area (3.5) of the second tube (3).

External pressure from pressing means (10) in the direction of the block arrows is exerted through the external tools (6, 7) to the corresponding tubes (2, 3), the assembly (1) passing from the first position to its second position.

The external pressure (10) exerted brakes the foil (4.4) through the second tube (3), when moving the assembly (1) from its first to its second position, thus providing of the necessary fluid communication between the first (2.2) and second (3.2) chambers of said assembly (1).

FIG. 6 also shows the external sensor (S), which is able to access the reading area (3.4) through the recessed area (4.3) of the connection tube (4) for reading the results of the lateral flow strip (SS).

Figure 7A:
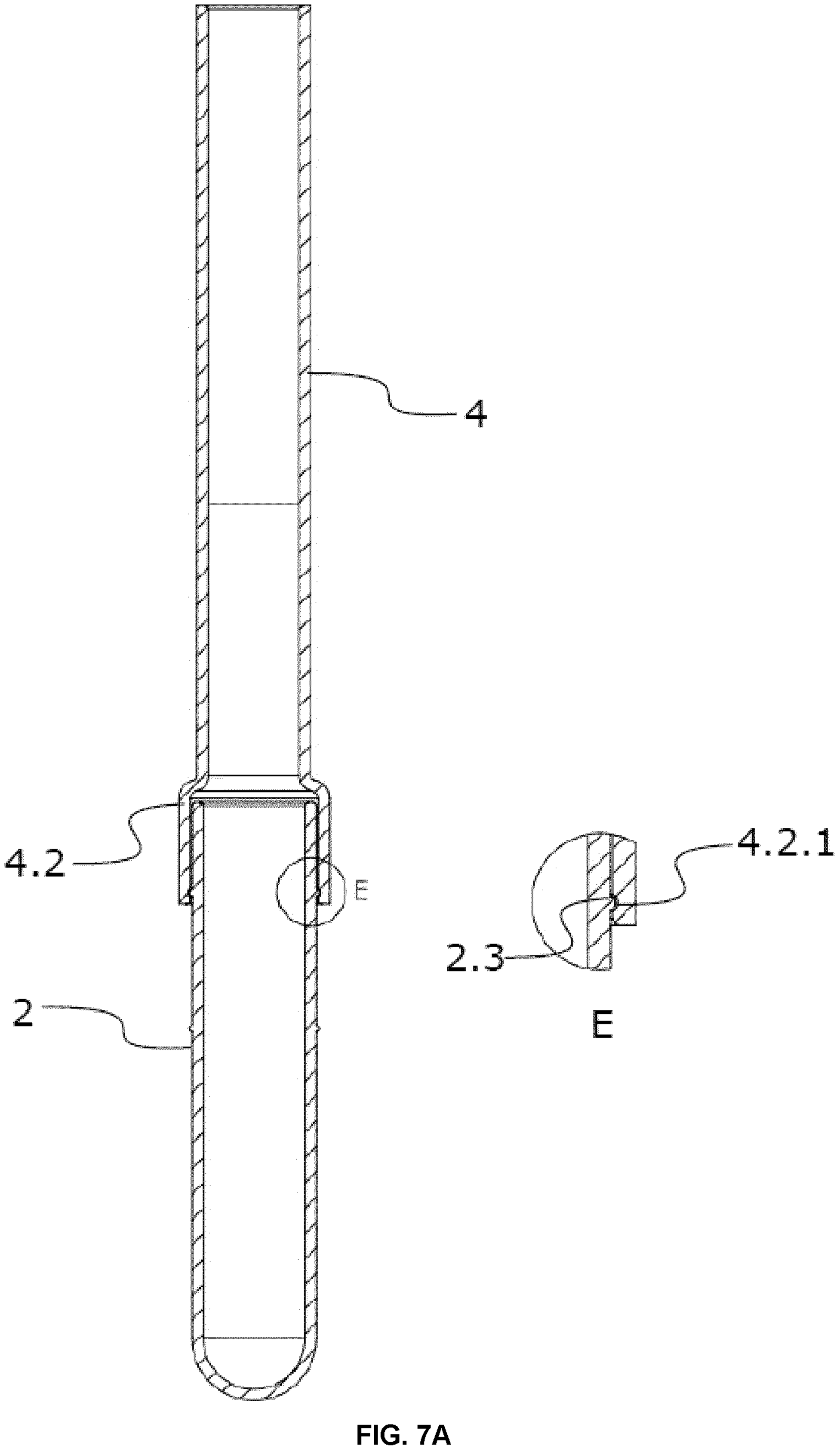
FIGS. 7A and 7B show, respectively, detailed views of the connection of elements present in the assembly of the kit of the sixth aspect of the invention.
Figure 7B:
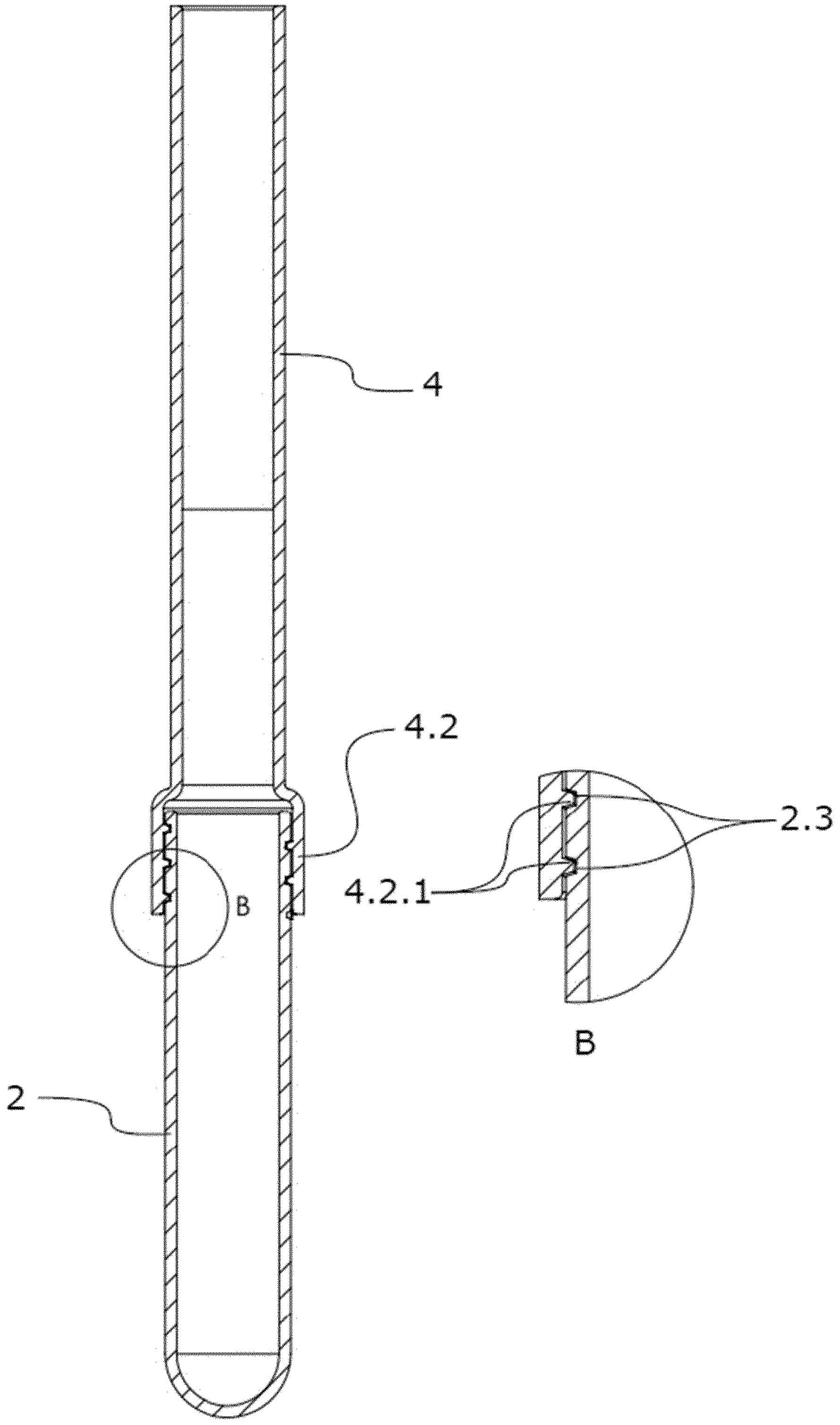

FIGS. 7A and 7B show detailed views of two different examples of connection between the first tube (2) and the connection tube (4).

Particularly, FIG. 7B shows the example mentioned in FIGS. 5A and 5B, wherein the coupling means (2.3, 4.2.1) of both tubes (2, 4) are embodied as a thread connection, as shown in detail B of FIG. 7B, which when mounted, provides a screwed-tight connection of both tubes (2, 4).

An alternative to such a connection can be found in FIG. 7A, wherein detail E shows the first tube (2), particularly a projection (2.3) formed on the outer surface of said first tube (2), which is housed in a groove (4.2.1) performed on the inner surface of the connection end (4.2) of the connection tube (4).

FIG. 8, as mentioned before, shows a reader (R) with a drawer (5), which allows housing several assemblies (1), configured as cassettes, inside.

Said assemblies (1) are introduced in its first position inside the drawer (5).

The reader (R) comprises reading means (8), not shown in the present figure as they are present inside the reader (R), and display means (11) which allow the user to consult the result of the lateral flow strip (SS), read by the external sensor (S) on the reading area (3.4) of the assembly (1) of the present embodiment.

Thus, each assembly (1) is introduced in the drawer (5) of the reader (R) in its first position, and the pressing means (10) of the first and/or second actuators (6, 7) exert a pressure on the corresponding tube (2, 3) of the assembly (1) in order to locate it in its second position, wherein the result of the analysis of the blood sample can be read by the external sensor (S).

An additional result can be shown in the display means (11), wherein the result read by the external sensor (S) is compared with a reference value established as a threshold value.

Therefore, according to the system shown in FIG. 8, a method for the preparation and reading of a blood sample by a reader (R) can be performed.

Particularly, a blood sample is introduced in the first chamber (2.2) of the first hollow tube (2).

After the present step, the assembly (1) is introduced inside the reader (R), between the first and second (6, 7) actuators of said reader (R). The blood sample along with the TLR4 agonist present in the first chamber (2.2) of the second tube (2) is then heated with the heating means (9) of the reader (R).

Afterwards, with the pressing means (10) of the first and/or second actuators (6, 7), the first hollow tube (2) is pressed against the second tube (3), breaking the foil (4.4) if present, and thus establishing a fluid communication between the first chamber (2.2) of the first hollow tube (2) and the second chamber (3.2) of the second tube (3) through the hole (3.1.1) causing the contact of the blood sample with the porous solid support (SS), That is, the assembly (1) is driven from its first position to its second position.

Once the blood sample has reached the porous solid support (SS), particularly the lateral flow strip, the reading means (8) of the reader (R) and the sensor (S) read the result present in the porous solid support (SS), through the reading area (3.4) and the reader (R) displays the result of said reading by means of the display means (11).

Additionally, a comparison of the result of the reading can be made with a reference value as already indicated before.

As explained above, the kit of the invention can be used to put into practice the methods of the invention. Therefore, in another aspect, the invention relates to the use of the kit of the invention for:

- detecting bacteremia in a subject,
- diagnosing sepsis in a subject suffering from systemic inflammatory response syndrome and/or
- diagnosing bacterial pulmonary exacerbation in a subject suffering from cystic fibrosis.

EXAMPLES

Patient Recruitment

The study was conducted in accordance with the ethical guidelines of the 1975 Declaration of Helsinki. All the participants provided written consent for the study. Septic suspected patients who fulfilled the diagnostic criteria for SIRS according to the Society of Critical Care Medicine and the European Society of Intensive Care Medicine international conferences were included in the study. Blood samples were collected at the time of admission, before any therapy, and sepsis was confirmed using clinical and analytical data. Note that the included patients were not on any type of intensive therapy, including pressors. Exclusion criteria: chronic inflammatory diseases (except asthma), presence of hematological malignancies, treatment with steroids and/or immunosuppressive drugs in the last month, previous presence of severe liver failure (serum aspartate aminotransferase and/or alanine aminotransferase>100 IU/L, prothrombin time<60% and total bilirubin<60 mmol/L), renal failure (plasma creatinine>200 μmol/L), HIV/AIDS, hepatitis B or C, and pregnancy.

Cytometric Bead Array

Tumor necrosis factor-α (TNFα), interleukin (IL)-1β, IL-6, IL-8, CCL-2 and IL-10 protein levels were determined using the Human Inflammatory cytometric bead array (CBA) kit (BD Biosciences), following the manufacturer's protocol. The samples were collected by flow cytometry using a BD FACSCalibur flow cytometer (BD Biosciences).

1. Quantification of Biomarkers after LPS Challenge

Septic suspected patients (n=25), grouped according hemocultive results, exhibit various states of activation after LPS challenge. TNFα, IL-1β, IL-6, IL-8, CCL-2 and IL-10 whole-blood production after ex vivo LPS stimulation (5 ng/mL, 2 h) were quantified by cytometric bead array. ***, p<0.005*, p<0.05 compare blood culture positive patients vs blood culture negative patients using unpaired t-test (FIG. 1) Serum PCR and Procalcitonine were measured in the same grouped patients following the standard biochemistry hospital assays (n=25) without any statistical significance between groups. (FIG. 1 Cont.)

2. Quantification of Biomarkers after LPS Challenge from Two *E. coli* and *B. abortus*

Figure 2:
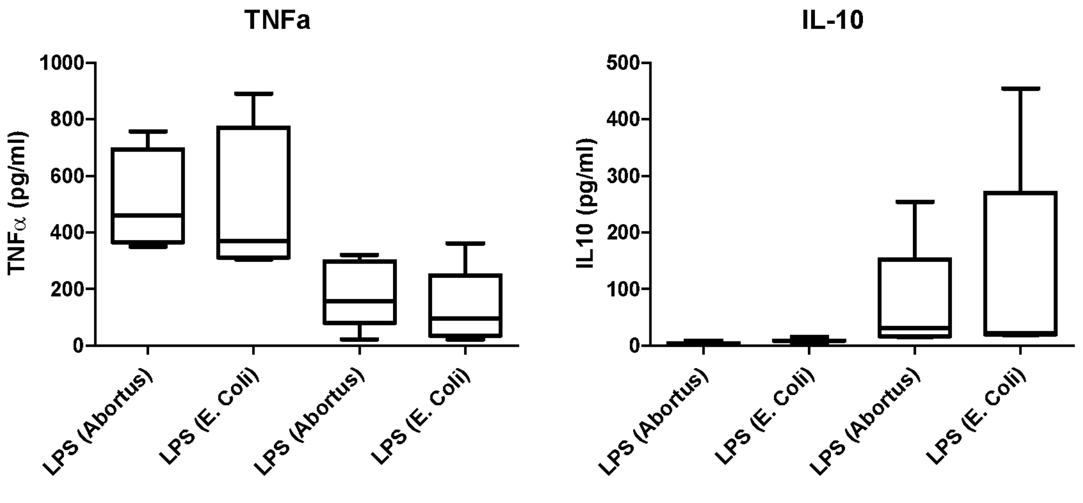
FIG. 2. Quantification of biomarkers after LPS challenge from two *E. coli* and *B. abortus*. TNFα and IL-10 whole-blood production after ex vivo *E. coli* and *B. abortus* LPS stimulation (5 ng/mL, 2 h) were quantified by cytometric bead array (n=25). ***, p<0.005*, p<0.05 compare blood culture positive patients vs blood culture negative patients using unpaired t-test.

TNFα and IL-10 whole-blood production after ex vivo *E. coli* and *B. abortus* LPS stimulation (5 ng/mL, 2 h) were quantified by cytometric bead array (n=25). ***, p<0.005*, p<0.05 compare blood culture positive patients vs blood culture negative patients using unpaired t-test. As shown in FIG. 2, no differences were obtained when different LPS compounds were used for the stimulation of the blood samples.

3. Diagnosis of Infection in Cystic Fibrosis (CF) Subjects

Cystic fibrosis (CF) is a progressive, genetic disease that causes persistent lung infections, limiting the ability to breathe over time. By the time symptoms appear, there is usually already significant lung damage. Respiratory infections further inflame the lungs, compromising breathing and causing further damage to lung tissue.

If these exacerbations can be predicted before the symptoms appear, they can be dealt with earlier, limiting their effect and the potential consequences. Being able to determine the immune status can help to determine. If the antibiotics are mandatory. The test will show a developing bacterial infection that will become a pulmonary exacerbation so it needs to be treated and studied (tested) to treat it the best way possible to avoid the pulmonary exacerbation consequences.

Targeted populations are Cystic fibrosis patients before and after being hospitalized for exacerbations (infections) and healthy volunteers, whom blood samples will serve to validate reference intervals of the two reference tests when the bacteremia is caused by a respiratory infection.

Patients Analyzed 14 non-smoker adults diagnosed with CF were studied on the basis of established criteria (clinical phenotype, sweat testing and CFTR genotyping), who had not used corticosteroids within the three months previous to the study. Exclusion criteria included a history of Chronic Obstructive Pulmonary Disease (COPD), asthma or other active lung disease, mental or physical handicap, or other significant diseases such as diabetes mellitus, congestive heart failure, ischemic or valvular cardiopathy or neuromuscular disease.

Additionally, six age-matched healthy volunteers without personal history of CF or other significant illness were included as controls. Septic patients were considered those with microbiologically confirmed bacteremia (positive blood cultures for *Escherichia coli*) secondary to urinary tract infection, who met the diagnostic criteria for sepsis by consensus conference definition.

Figure 3:
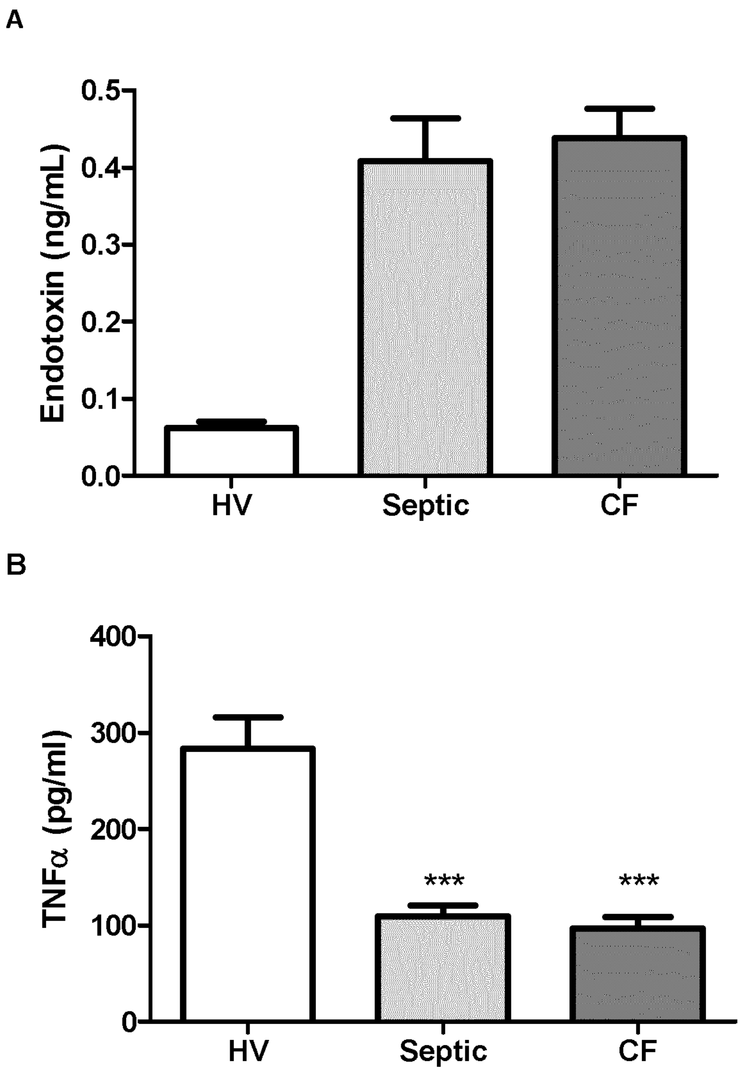
FIG. 3. Diagnosis of infection in Septic and Cystic fibrosis (CF) subjects. A. Levels of LPS were tested by LAL kit in serum. B. Quantification of TNF-alpha whole-blood production after ex vivo *B. abortus* LPS stimulation (5 ng/mL, 2 h) were quantified by cytometric bead array (n=14). ***, p<0.005 compare Septic and CF patients vs Healthy Volunteers (HV) using unpaired t-test.

TNFα whole blood production from patients with CF (n=14) and HV (n=6) exhibit various states of activation after LPS challenge (5 ng/mL, 2 h). The cytokines were quantified by cytometric bead array. *, $p<0.005$ compare CF patients vs HV using unpaired t-test (*, $p<0.005$ compare CF patients vs HV using unpaired t-test) (FIG. 3).

Endotoxin Quantification to Confirm Blood-Infection

The LPS concentrations were determined in 200 ml of plasma using a kit based on a *Limulus* amaebocyte extract (Chromogenic Endotoxin Quant Kit). Determinations were done five times per sample.

Method Protocol

Tumor necrosis factor-α (TNFα) were determined using the Human Inflammatory cytometric bead array (CBA) kit (BD Biosciences), following the manufacturer's protocol. The samples were collected by flow cytometry using a BD FACSCalibur flow cytometer (BD Biosciences).

4. Specific Biomarker Expression Levels in Bacteremia According to the Origin of the Infection Septic patients (n=50), grouped according the source of their primary infection, exhibit various states of activation after LPS challenge. TNFα and IL-10 whole-blood production after ex vivo LPS stimulation (5 ng/mL, 2 h) were quantified by cytometric bead array. *, $p<0.05$ compare respiratory source vs abdominal or urinary using unpaired t-test (FIG. 9).

Figure 9:
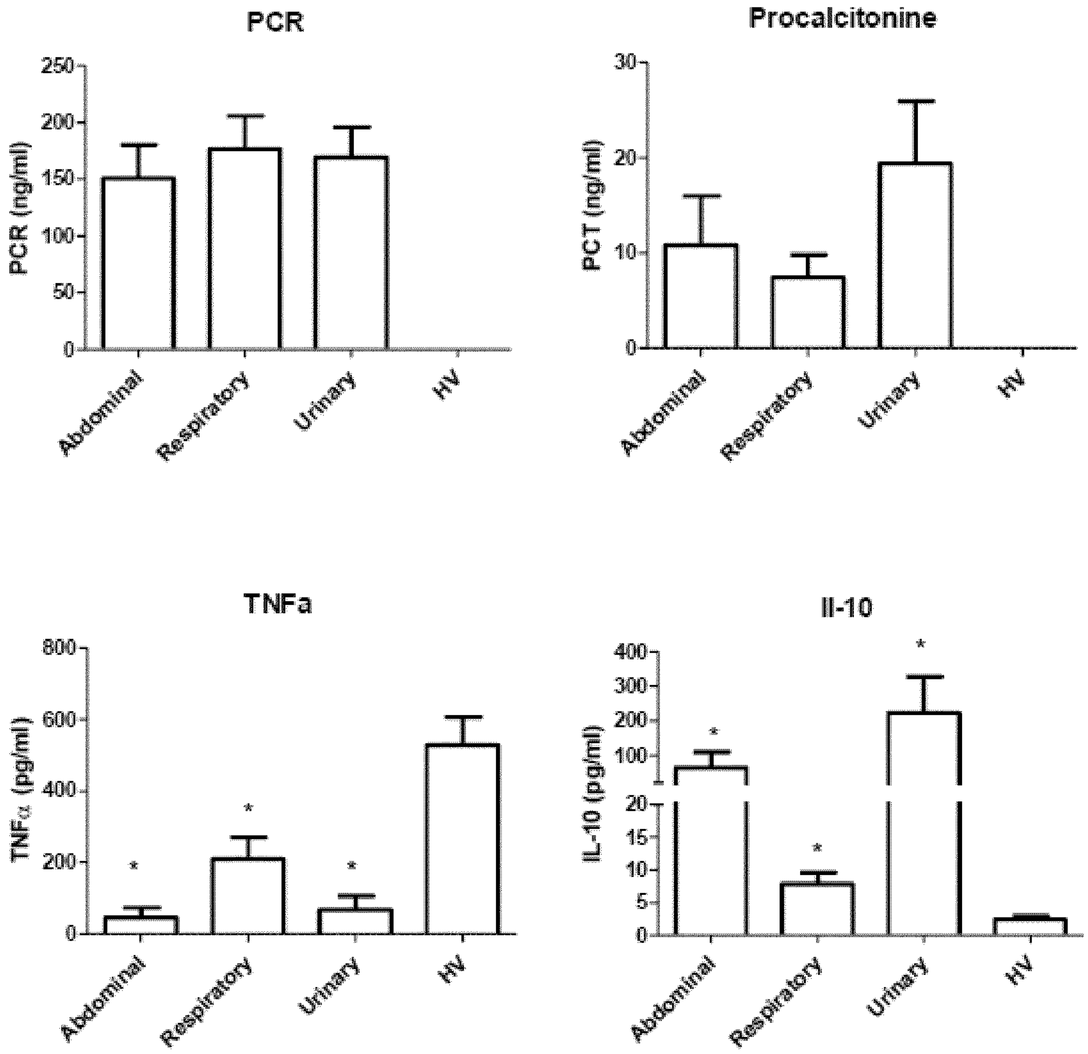
FIG. 9. Diagnosis of infection source in Septic subjects. TNFα, IL-10, serum PCR and procalcitonine whole-blood production after ex vivo were quantified by cytometric bead array (n=50). *, p<0.05 compares respiratory source vs abdominal or urinary using unpaired t-test.

Serum PCR and Procalcitonine were measured in the same grouped patients following the standard biochemistry hospital assays without any statistical significance between groups (FIG. 9).

5. Specificity Assay to Test Biomarker Production with Different TLR Stimulators Blood samples from 5 healthy donors were stimulated with different TLR specific agonists (LPS, TLR4 specific; x-1 and x-2, TLR2-TLR6 specific; K and I, TLR2-TLR4 specific); for 3 hours, and then TNFα levels were analyzed. X-1 and x-2 agonists are purified preparations of lipoarabinomannan (LTA)-like components, and, K and I are purified preparations of lipopolysaccharides (LPS) and peptidoglycan (PGN)-like components.

Figure 10:
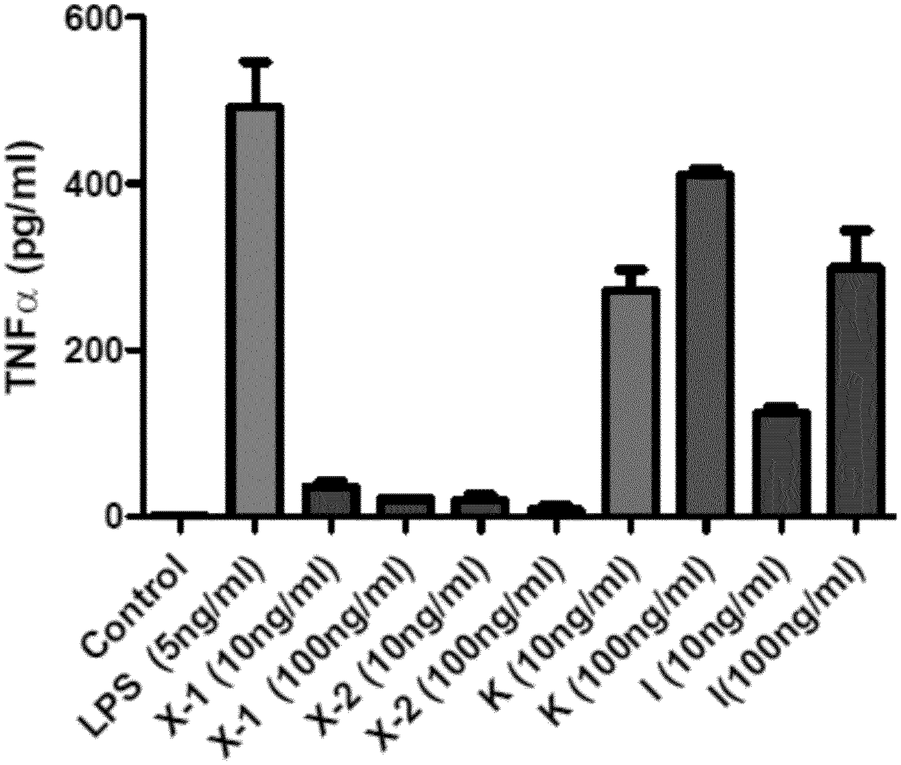
FIG. 10. Healthy donors exhibit various activation levels and biomarker production after different stimulator challenges. TNFα production (pg/mL) after 3 hours of ex vivo stimulation: [LPS, 5 ng/ml, TLR4 specific]; [x-1 and x-2, 10 and 100 ng/ml, TLR2-TLR6 specific]; [K and Y, 10 and 100 ng/ml, TLR2-TLR4 specific] from Whole blood from 5 healthy donors.

As it is shown in FIG. 10, the specific TLR4 agonist LPS was able to induce the production of significant levels of TNFα, while the non TLR4 agonists, that is, x-1 and x-2, hardly induced the production of the cytokine and the non-specific agonists, K and I, did not elicit such a remarkable increase in the production of TNFα, even at higher concentrations than LPS. This demonstrates that only TLR4 agonists are able to provide results in a diagnostic method to differentiate healthy donors from septic potential patients.

The invention claimed is:

1. A kit comprising a reagent specific for determining the expression level of at least one gene selected from the group consisting of tumour necrosis factor alpha (TNFα), IL-1b, IL-10, CCL2, interferon beta (IFN-β), IL-17, IL-2, IL-4 and VEGF, further comprising a TLR4 agonist;

wherein the reagent comprises nucleic acid probes capable of specifically hybridizing to the gene of interest, PCR primers capable of specifically amplifying the gene of interest, or antibodies or aptamers capable of specifically binding to the expression product of the gene of interest, and wherein the kit further comprises an assembly for the analysis of a blood sample, configured for being housed in a reader, the assembly comprising:

a first hollow tube comprising an open end, the first hollow tube extending along a longitudinal direction X-X', the first hollow tube further comprising:

a first chamber configured to house the blood sample and containing the TLR4 agonist, and first coupling means located in the open end, a second housing extending along the longitudinal direction X-X' and comprising a guided end, the second housing further comprising:

a second chamber containing at least one antibody that specifically binds to the protein encoded by the gene, wherein the antibody is immobilized on a porous solid support, a connection tube extending along the longitudinal direction X-X' and comprising a guiding end and a connection end, the connection end comprising second coupling means, wherein the connection tube houses the second housing, guiding its movement along the longitudinal direction X-X' such that the second housing partially enters into the first chamber of the first hollow tube, thus establishing a fluid communication path between said first chamber of the first hollow tube and the second chamber the second housing.

2. The kit according to claim 1, wherein the reagent specific for determining the expression level of at least one gene is an antibody which specifically binds to the protein encoded by said gene.

3. The kit according to claim 2, further comprising a culture medium and/or an anticoagulant and/or a reagent specific for determining the expression level of at least one additional gene selected from the group consisting of the genes:

Brain-Derived Neurotrophic Factor (BDNF), Eotaxin-1, Factor VII, Granulocyte-Macrophage Colony-Stimulating Factor (GM-CSF), soluble Intercellular Adhesion Molecule 1 (sICAM-1), interferon gamma (IFNG), interleukin-1 alpha (IL-1A), interleukin-1 receptor antagonist (IL-1RA), interleukin-3 (IL-3), interleukin-5 (IL-5), interleukin-7 (IL-7), interleukin-15 (IL-15), interleukin-18 (IL-18), interleukin-23 (IL-23), Macrophage Inflammatory Protein-1 alpha (MIP-1A), Macrophage Inflammatory Protein-1 beta (MIP-1B), Matrix Metalloproteinase-3 (MMP3), Matrix Metalloproteinase-9 (MMP9), Stem Cell Factor (SCF) and Tumor Necrosis Factor beta (TNF-B).

4. The kit according to claim 1, wherein the TLR4 agonist is lipopolysaccharide (LPS).

5. The kit according to claim 1, wherein the second tube of the assembly further comprises a foil, located at the connection end of the connection tube, which blocks the communication between the first hollow tube and the second housing tube, thus avoiding the fluid communication between first chamber of the first hollow tube and the second chamber of the second housing tube through said hole.

6. The kit according to claim 1, wherein the second coupling means cooperate with the first coupling means detachably fixing the connection tube and the first hollow tube of the assembly.

7. The kit according to claim 1, wherein the second housing tube of the assembly comprises a receiving end, opposite the guided end, the receiving end comprising a pressing area which is configured to be externally pressed.

8. The kit according to claim 1, wherein the second housing is tubular and the guided end has a hole, such that when the second housing partially enters into the first chamber of the first hollow tube, a fluid communication path between said first chamber of the first hollow tube and the second chamber of the second housing is established through the hole.

9. A method for treating a subject suspected of suffering from bacteremia, the method comprising the steps of:
determining whether the subject has bacteremia by:
a) contacting a blood sample from the patient with a TLR4 agonist in the presence of an anticoagulant;
b) determining the expression level of at least one gene selected from the group consisting of tumour necrosis factor alpha (TNFα), IL-1b, IL-10, CCL2, interferon beta (IFN-ß), IL-17, IL-2, IL-4 and VEGF in the blood sample previously contacted with the TLR4 agonist;
wherein steps (a) and (b) are carried out by using the kit according to claim 1, and
c) comparing said level with a reference value;
wherein
a decreased level of TNFα, IL-1b, IL-17 and/or IFN-β compared to the reference value and/or
an increased level of IL-10, CCL2, IL-2, IL-4 and/or VEGF compared to the reference value
is indicative of the presence of bacteremia in the subject; and wherein if the subject has bacteremia, the method comprises administering one or more broad spectrum antibiotics.

10. The method according to claim 9, wherein
(A) the subject suffers from systemic inflammatory response syndrome (SIRS), and wherein
a decreased level of TNFα, IL-1b, IL-17 and/or IFN-B compared to the reference value and/or—an increased level of IL-10, CCL2, IL-2, IL-4 and/or VEGF compared to the reference value is indicative of sepsis;
and if the subject suffers from sepsis, then the method comprises administering one or more broad spectrum antibiotics; and
if the subject does not suffers from sepsis, then the method comprises administering a therapy for SIRS
or wherein
(B) the subject suffers from cystic fibrosis (CF), and; wherein
a decreased level of TNFα, IL-1b, IL-17 and/or IFN-β compared to the reference value and/or
an increased level of IL-10, CCL2, IL-2, IL-4 and/or VEGF compared to the reference value is indicative of the presence of bacterial pulmonary exacerbation in the subject; and if the subject has bacterial pulmonary exacerbation and is not under treatment with an antibiotic, then the method comprises administering one or more broad spectrum antibiotics; and
if the subject has bacterial pulmonary exacerbation and is under treatment with an antibiotic, then the method comprises administering an increased dosage of said antibiotic or administering a different type of antibiotic; and if the subject does not have bacterial pulmonary exacerbation, then the method comprises administering a therapy for cystic fibrosis.

11. The method according to claim 9, wherein the subject diagnosed with bacteremia, sepsis or bacterial pulmonary exacerbation, experience a heath improvement or amelioration of the symptoms within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours after the collection of the blood sample.

12. The method according to claim 9, wherein the method further comprises determining the expression level of at least one additional gene selected from the group consisting of BDNF, Eotaxing-1, Factor VII, GM-CSF, SICAM-1, IFNG, IL-1A, IL-1RA, IL-3, IL-5, IL-7, IL-15, IL-18, IL-23, MIP-1A, MIP-1B, MMP3, MMP9, SCF and TNF-B.

13. The method according to claim 9, wherein the determination of the expression level of the gene is carried out by determining the levels of the mRNA of the gene or by determining the levels of the protein encoded by said gene.

14. The method according to claim 9, wherein the TLR-4 agonist is an endotoxin.

15. The method according to claim 9, wherein the determination of the expression level of the at least one gene is performed after the blood sample is contacted with the TLR-4 agonist for a period of time between 1 and 3 hours.

16. The method according to claim 9, wherein the blood sample that is contacted with the TLR-4 agonist is a whole blood sample.

17. The method according to claim 9, wherein after step (a), the blood sample is separated into cells and plasma, and wherein the determination of the expression level of the at least one gene is carried out by determining the levels of the mRNA of said gene in the cells and/or by determining the levels of the protein encoded by said gene in the plasma.

18. The method according to claim 9, wherein the administration of a therapy is commenced within less than 24 hours, suitable within 22 hours, within 20 hours, within 18 hours, within 16 hours, within 14 hours, within 12 hours, within 20 hours, within 18 hours, within 16 hours, within 14 hours, within 12 hours, within 10 hours, within 8 hours, within 6 hours, within five hours, suitably within four hours, suitably within three hours following obtaining said blood sample.

* * * * *